(12) United States Patent
Kaplan et al.

(10) Patent No.: US 8,293,486 B2
(45) Date of Patent: Oct. 23, 2012

(54) FUNCTIONALIZATION OF SILK MATERIAL BY AVIDIN-BIOTIN INTERACTION

(75) Inventors: David L. Kaplan, Concord, MA (US); Xiaoqin Wang, Winchester, MA (US); Monica A. Serban, Melrose, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 13/381,687

(22) PCT Filed: Jul. 20, 2010

(86) PCT No.: PCT/US2010/042502
§ 371 (c)(1),
(2), (4) Date: Feb. 9, 2012

(87) PCT Pub. No.: WO2011/011347
PCT Pub. Date: Jan. 27, 2011

(65) Prior Publication Data
US 2012/0129255 A1    May 24, 2012

Related U.S. Application Data

(60) Provisional application No. 61/227,254, filed on Jul. 21, 2009.

(51) Int. Cl.
*G01N 33/53* (2006.01)
*C07K 1/00* (2006.01)

(52) U.S. Cl. .......................................... 435/7.1; 530/350
(58) Field of Classification Search .................. 435/7.1; 530/350
See application file for complete search history.

(56) References Cited

U.S. PATENT DOCUMENTS

| 6,287,792 B1 | 9/2001 | Pardridge et al. |
| 2004/0102369 A1 | 5/2004 | Wu et al. |
| 2008/0085272 A1 | 4/2008 | Kaplan et al. |

FOREIGN PATENT DOCUMENTS

WO   2008/118133   10/2008

*Primary Examiner* — Maryam Monshipouri
(74) *Attorney, Agent, or Firm* — Nixon Peabody LLP; David S. Resnick

(57) ABSTRACT

The present invention provides for compositions and methods of linking silk fibroin to active agents through the specific interaction between avidin and biotin, providing for functionalization of silk-based protein biomaterials. An avidin- or biotin-modified silk is a biomaterial platform for functionalization with a variety of correspondingly linked active agents, such as antibodies and growth factors. A variety of functionalized silk materials, such as silk hydrogel, silk micro/nanoparticles and silk films, can be prepared by the methods of the present invention. The functionalization strategies of the present invention are relatively easy, fast and feasible, and are thus useful in many biomedical applications.

14 Claims, 8 Drawing Sheets

FUNCTIONALIZATION OF SILK MATERIAL BY AVIDIN-BIOTIN INTERACTION

CROSS REFERENCE TO RELATED APPLICATIONS

This application is a 35 U.S.C. §371 National Phase Entry Application of International Application No. PCT/US2010/042502 filed Jul. 20, 2010, which designates the U.S., and which claims benefit under 35 U.S.C. §119(e) of U.S. Provisional Application Ser. No. 61/227,254 filed Jul. 21, 2009, the contents of which are incorporated herein by reference in its entirety.

GOVERNMENT SUPPORT

This invention was made with support from the federal government under grant No. P41 EB002520, awarded from the NIH Tissue Engineering Resource Center. The U.S. government has certain rights in the invention.

FIELD OF THE INVENTION

The present invention relates to drug and biologics delivery, tissue engineering, and regenerative medicine. More specifically, the present invention provides for both methods of functionalizing silk fibroin via Avidin-Biotin linkages and the silk materials resulting there from. The functionalized silk materials are useful, for example, as scaffolds for the encapsulation and delivery of active agents.

BACKGROUND

The functionalization of biomaterials with tissue regeneration-relevant growth factors and cell surface-recognizing antibodies is a rapidly growing area in drug delivery, tissue engineering and regenerative medicine in general. The therapeutic value of these biomaterials is increased by their ability to target specific tissues, cells or disease site, through the surface modification of the carrier with specific molecules, which specifically bind to the cancerous tissues and cells. For example, monoclonal antibodies may be linked to the surface of the carrier and act against antigens on target cells. Among these biomaterials, silk fibroin is recognized as versatile and useful FDA-approved biomaterial that can be utilized for drug delivery. Silk fibroin can be coupled with various biomolecules, such as bone morphogenetic protein 2 to induce bone formation, or RGD peptide to promote cell attachment, via carbodiimide-mediated reactions. Direct covalent coupling may negatively impact the bioactivity of the biomolecules, however, due to the reactions at amine groups. Hence, there is a need for a new strategy to bind bioactive molecules to silk that not only reduces the activity loss of bioactive molecules, but also increases the binding specificity and efficiency.

Further, the current functionlization techniques are mainly surface functionalization of polymerized material by simply immersing the material in the solution or solvent containing the functional group. Incorporation of functional groups within a bulk material, however, is superior to the surface functionalization in many applications. For example, in cartilage and soft tissue engineering applications, functionalization of the bulk material enables encapsulated cells to grow and differentiate in a sustained and homogeneous manner under the support of surrounding high-density functional groups in three dimensions. Hence it is desirable to functionalize the silk in a manner so that it may be further fabricated into different material formats, such as hydrogels, nano/microparticles, as useful scaffolds for encapsulation and delivery of cells or active agents.

SUMMARY

The present invention functionalizes silk fibroin, providing methods for linking silk fibroin to active agents through a highly specific interaction between avidin and biotin, thus broadening the horizons for functionalized silk-based protein biomaterials. An avidin- or biotin-modified silk is used as a biomaterial platform for functionalization with a variety of biotin- or avidin-linked active agents, such as antibodies, cytokines, and/or growth factors. A variety of functionalized silk materials can be prepared by the methods of the present invention. The functionalization strategies of the present invention are easy, fast and feasible, and are thus useful in many biomedical applications. For example, the biomaterials of the present invention can be used to protect drug activity, change its administration rout, and/or improve its in vivo efficacy.

Some embodiments of the present invention provide for methods of functionalizing a silk fibroin protein with an active agent in aqueous solution, comprising the steps of: reacting a silk fibroin protein molecule with avidin in an aqueous solution to form a silk fibroin protein-avidin conjugate, wherein avidin is linked to the silk fibroin protein through a covalent bond; providing a biotinylated active agent; and contacting the silk fibroin protein-avidin conjugate with the biotinylated active agent to form a silk fibroin protein-avidin-biotin-agent conjugate, wherein the biotinylated active agent is linked to the silk fibroin protein-avidin conjugate through avidin-biotin interaction. The avidin can be but is not limited to, for example, avidin, NeutrAvidin, CaptAvidin, or streptavidin.

The present invention also provides for an active agent-functionalized silk material in a variety of formats, e.g., hydrogels, films, diazo-silk films, porous sponge scaffolds, electrospun scaffolds, nano/micro particles, or combinations of these, comprising silk fibroin molecules functionalized with an active agent. In some embodiments, the silk material of the invention is prepared from an aqueous silk fibroin solution (bulk solution). The bulk silk fibroin protein molecules in the silk fibroin solution are linked to an active agent through avidin-biotin linkage.

Some embodiments of the present invention also provide for a method of functionalizing the surface of a silk particle with an active agent, comprising providing a silk particle; providing a biotinylated active agent; reacting the silk particle with avidin in an aqueous solution to form a silk particle-avidin conjugate, wherein avidin is linked to the silk particle through a covalent bond; contacting the silk particle-avidin conjugate with the biotinylated active agent to form a silk particle-avidin-biotin-active agent conjugate, wherein the biotinylated active agent is linked to the silk particle-avidin conjugate through avidin-biotin interaction.

For example, embodiments provide carbodiimide-based coupling of NeutrAvidin to silk fibroin in solution or in microsphere format, and the subsequent binding of biotinylated biomolecules to silk materials. Silk microspheres have been functionalized with anti-CD3 antibody for targeting the microspheres to a $CD3^+$ T-cells. A particular embodiment provides for a composition comprising biotinylated antibody-avidin-silk microspheres, wherein the antibody-loaded microspheres are capable of binding to cell-surface antigens. In other embodiments, silk films and diazo-silk films have been functionalized with anti-GFP antibody.

Moreover, to minimize non-specific binding of bioactive agents to silk, different functionalization strategy may be used. For example, instead of direct avidin coupling to silk fibroin, biotin may be coupled to the silk fibroin proteins or the surface of the silk particles, and avidin-biotinylated active agents may be added subsequently, thus forming a conjugate of silk biotin-avidin-biotinylated active agent.

DESCRIPTION OF THE DRAWINGS

FIG. 3A shows a pretreatment using BSA: Silk microspheres were incubated overnight with 10 mg/ml BSA, then the microspheres were reacted with 25 µg/ml HRP-conjugated NeutrAvidin. The amount of bound NeutrAvidin was determined by measuring HRP activity. FIG. 3B shows posttreatment using Triton X-100 detergent: HRP-NeutrAvidin-coupled microspheres were washed thrice in a 1% (v/v) Triton X-100 solution, followed by the same HRP activity determination. Data are shown as means±standard deviation (n=4). * and ** indicate significant ($p \leq 0.05$) and very significant ($p \leq 0.01$) differences between samples, respectively.

FIGS. 4A and 4B show control cells: human bone marrow-derived mesenchymal stem cells (hMSCs). FIGS. 4C-4F show CD3$^+$ T-cells. FIGS. 4A, 4C, and 4E are images of phase contrast microscopy. FIGS. 4B, 4D, and 4F are images of confocal laser scanning fluorescence microscopy. Gray arrows indicate the lymphocytic cells and white arrows indicate the free microspheres. Scale bar=10 µm in FIGS. 4A, 4B, 4E and 4F; 50 µm in FIGS. 4C and 4D.

FIGS. 7A and 7B: Silk microspheres after mixing with TMR-BSA without washing steps. FIGS. 7C and 7D: same microspheres after washing three times with water. Scale bar=10 µm in FIGS. 7A and 7C; 2 µm in FIGS. 7B and 7D. The binding of TMR-BSA to silk microspheres was concentration dependent, as determined by measuring the unbound species remained in the supernatants (FIG. 7E).

DETAILED DESCRIPTION

Figure 1:
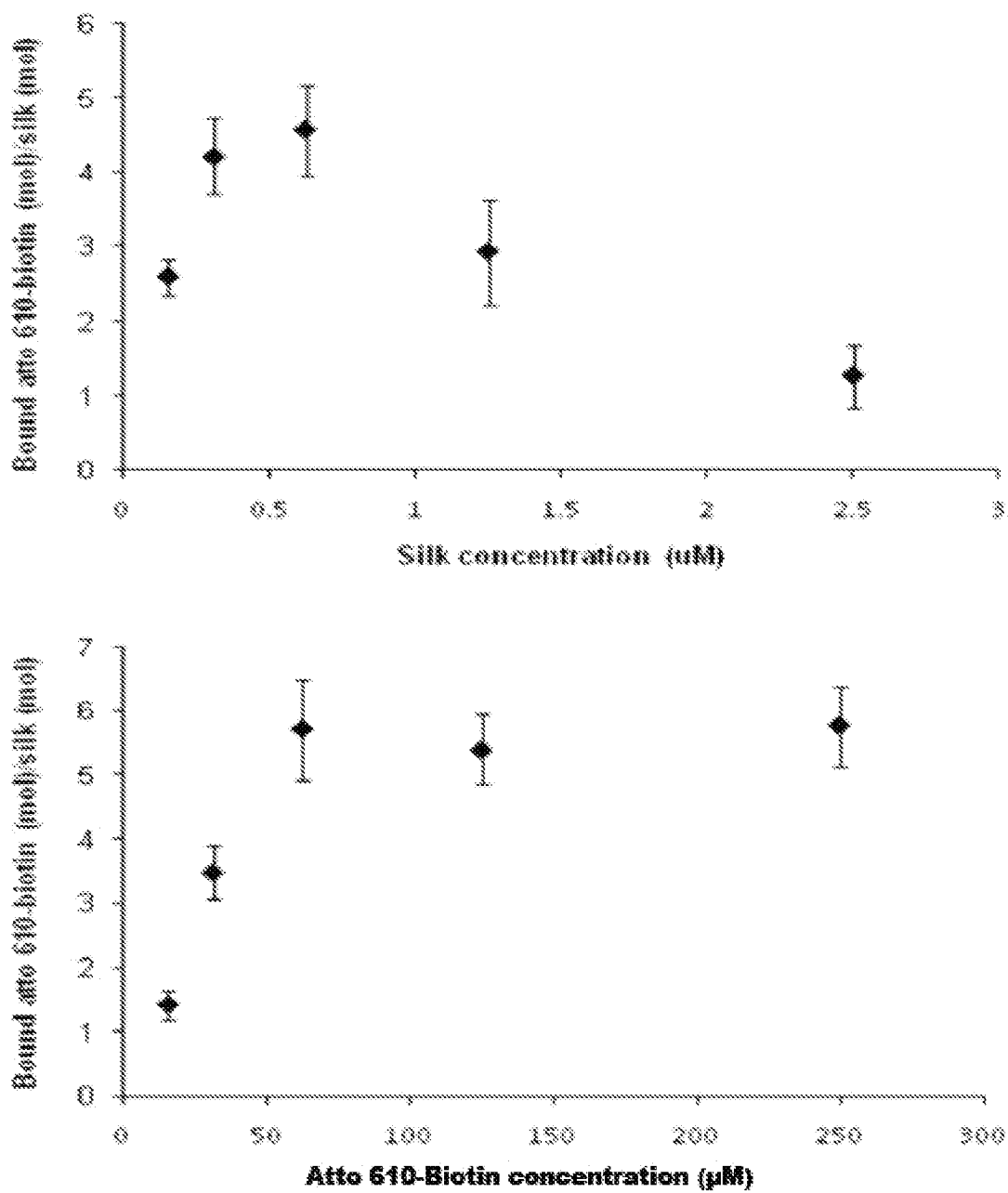
FIG. 1 shows the stoichiometry of bound NeutrAvidin on silk. NeutrAvidin-coupled silk solution was induced to gel by sonciation, and the NeutrAvidin in the gel was quantified by interaction with Atto 610-Biotin and measuring absorbance at 610 nm. Top panel: Atto 610-Biotin concentration was kept constant while the silk concentration was varied. Bottom panel: silk concentration was kept constant while the Atto 610-Biotin concentration was varied.

The present invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Controlled drug release and targeted drug delivery are growing areas of research with consistent focus on developing and characterizing polymer matrix systems useful in regulating the release of drugs in a consistent and predictable manner. Chen & Mooney, 20 Pharm. Res. 1103 (2003). Materials used as drug delivery carriers include chemically synthesized polymers and natural polymers. These materials can be fabricated and used as hydrogel, nano/microparticles, and other material formats. Hydrogels contain high water content (usually >30%), and are thus considered useful for encapsulation and delivery of cells and bioactive molecules (i.e., active agents), in applications such as tissue engineering and cell therapeutics. Park & Lakes, BIOMATS. INTRO. (2nd ed., Plenum Press, NY, 1992). Microparticles, usually microspheres (1 μm to 1000 μm), can be loaded with drug via physical entrapment or covalent coupling. Chen & Mooney, 2003. Drug is then released through passive diffusion from the pores of the material matrix or as the matrix itself degrades. Currently, gelatin, alginate, collagen, and the synthetic polymer PLGA (poly-lactic, glycolic acid) have been extensively explored as materials for hydrogels and microparticles in the context of drug release. Bala et al. 21 Crit. Rev. Ther. Drug Carrier Sys. 387 (2004); Dinauer et al., 26 Biomats. 5898 (2005).

Besides tissue engineering, functionalized biomaterials also have broad applications in pharmaceuticals for disease treatments. Therapeutic drugs, from small molecules to macromolecule drugs, can be incorporated into a biomaterial matrix via covalent or non-covalent linkages, or physical entrapment. The biomaterial is used as a drug carrier to protect the drug activity, change its administration rout, and improve its in vivo efficacy. The therapeutic value of biomaterials used as drug delivery carriers is increased by their ability to be targeted to specific tissues, allowing controlled release to occur at the targeted cells or disease site. Dinauer et al., 2005. In cancer therapy, many chemotherapy drugs affect both tumor and normal cells. Specifically targeting the drug to cancerous tissues and cells can increase the drug concentration in the target tissue, thereby increasing the effectiveness of the treatment. Bala et al., 2004. The specific targeting may be achieved by linking the surface of the carrier with specific molecules, which then act against marker molecules on the target cell. For example, monoclonal antibodies may be linked to the surface of the carrier and act against marker antigens on the target cells. Among various technologies being used for surface modification, the non-covalent avidin-biotin linkage system has attracted significant interest due to the simplicity and versatility of the system, high binding affinity, physiological reaction conditions and commercial availability of biotinylated or streptavidin-conjugated biomolecules. Diamandis et al., 37 Clin. Chem. 625 (1991); Chen et al., 50 Drug Dev. Res. 258 (2000).

Additionally, functionalization of biomaterials with tissue regeneration-relevant growth factors and cytokines is an area of strong interest. Chen & Mooney, 2003. Active agents are linked to biomaterials via different techniques, including covalent linkages and non-covalent interactions, depending on impact of bioactivity or goals for release of the active agent. After being implanted in vivo, these bioactive additions influence cell functions such as growth and differentiation, and regulate tissue formation or remolding. For non-covalent coupling, control of release rate through optimization of diffusion or material degradation facilitates access of the bioactive agents to target cells at a sufficient dose within a desired time range. These are properties in regulation of release profiles that covalent linkages usually lack because of the state of immobilization.

Among various technologies being used for linking functional groups to biomaterials, the avidin-biotin non-covalent linkage system has attracted significant focus due to the simplicity and versatility of the system. Avidin, or its derivatives (e.g., NeutrAvidin, CaptAvidin, streptavidin) can be linked covalently to nano- or microspheres. Dinauer et al., 2005. Avidin is a glycoprotein found in the egg white and tissues of birds, reptiles, and amphibia. This protein contains four identical subunits (four biotin binding sites), has a combined mass of ~67 KDa and a cationic isolectric point of ~10. NeutrAvidin is a deglycosylated form of avidin, having a mass of ~60 KDa and high biotin-binding affinity ($K_a = 10^{15}$ $M^{-1}$)[1]. NeutrAvidin has a neutral isoelectric point, minimizing nonspecific adsorption, along with lysine residues that remain available for derivatization or conjugation. NeutrAvidin yields a low nonspecific binding among the known biotin-binding proteins, having a specific activity for biotin-binding of about 14 μg/mg of protein: nearly the theoretical maximum. Streptavidin has a mass of ~53 KDa, an isoelectric point between ~6.8 to ~7.5, and its specificity lies in between that of avidin and NeutrAvidin.

Due to the high affinity of avidin for biotin ($K_D = 10^{-15}$ M), biotinylated molecules can be coupled rapidly to nano/microsphere particles under mild conditions (neutral pH, room temperature). Dinauer et al., 2005; Diamandis et al., 1991; Chen et al., 2000. Numerous biotinylated proteins and non-protein therapeutics are available. Similarly, avidin or its derivatives, can be linked covalently to a polymer matrix, such as a film or a hydrogel, so that biotinylated biomolecules can be linked and immobilized in the gel matrix. This provides a convenient option to functionalize biomaterials, and may further be used to promote tissue repair or regeneration, such as wound healing. Boyce et al., 37 Antimicro. Agents Chemother. 1890 (1993); Burnham et al., 27 Biomats. 5883 (2006); Chen et al., 50 Drug Devel. Res. 258 (2000); Clapper et al., 9 Biomacromol. 1188 (2008); Hynd et al., 81 J. Biomed. Mater. Res. A 347 (2007a); Hynd et al., 162 J. Neurosci. Meths. 255 (2007b).

Among various covalent coupling strategies, carbodiimide-based reactions have been widely used to link the carboxyl groups on material surfaces and the amine groups (e.g., lysine residues) on avidin molecules. The strategy has been studied in detail in the literature using two different materials with extensive carboxyl groups on their surfaces. Vermette et al., 259 J. Colloid. Interface Sci. 13 (2003). It was also compared with the affinity "docking" strategy of using a surface-attached biotinylated poly(ethylene glycol) that could bind one side of NeutrAvidin, allowing the other side to interact with biotinylated biomolecules. The carbodiimide-immobilized NeutrAvidin barely lost its biotin binding ability when compared to the control sample, indicating that the lysine residues involved in the reaction were not situated close to the binding pockets. The carbodiimide coupling strategy resulted in a greater amount of biotinylated molecules bound to the material surfaces when compared to the affinity "docking" strategy, although the nonspecific binding background was also higher (up to 70% of the total binding). Vermette et al., 2003.

Silk is a versatile and useful FDA-approved biomaterial that can be utilized for controlled drug release because of its self-assembly into materials, formation of materials with high mechanical strength, extensive natural and physical cross-linking, and fairly slow enzymatic degradation in vivo. Altman et al., 24 Biomats. 401 (2003). Silk Fibroin is the structural protein found in silk fibers which can self-assemble into a β-sheet rich structure. Kaplan et al., 544 SILK POLYMERS: MATS. SCI. & BIOTECH. (Am. Chem. Soc. Symposium Series, ed., Washington, D.C., 1994); Kaplan et al., SILK IN PROTEIN-BASED MATS. 103 (Birkhäuser, Boston, Mass., 1997). Silk fibroin has been used in a number of biomaterial applications, such as tissue engineering porous scaffolds (Nazarov et al., 5 Biomacromol. 718 (2004); Kim et al., 26 Biomats. 2775 (2005)), films (Jin et al., 5 Biomacromol. 711 (2004); Jin et al., 15 Adv. Funct. Mats. 1241 (2005)), hydrogels (Wang et al., 29 Biomats. 1054 (2008)), and microspheres (Wang et al., 117 J. Control. Release 360 (2007)). See also, e.g., WO 04/000,915; WO 04/062,697; WO 05/012,606; WO 08/150,861; WO 08/118,133; PCT/US2010/041953. All of these materials display high mechanical strength, biocompatibility, and biodegradability, therefore suitable for cell and biomolecule encapsulation. Compared to other degradable polymeric biomaterials for microparticle and hydrogel systems, a significant advantage of silk fibroin is its ability to naturally and physically crosslink via the formation of crystalline β-sheet structural networks. Kaplan et al., 1994; Kaplan et al., 1997. The extent to which this physical network forms directly relates to the mechanical properties and rates of degradation of the material. Wang et al., 2008; Wang et al., 2007.

Many other polymeric biomaterial systems either require chemically crosslinking reactions to stabilize the polymeric materials (e.g., collagens, gelatins), or must be processed in organic solvents to generate drug delivery carrier systems (e.g., PLGA), thus limiting the utility. Silk, however, can be processed at ambient conditions in water to achieve the material requirements, hence avoiding the above limitations. Silk proteins are commonly produced by insects and spiders, form fibrous materials in nature. Kaplan et al., ACS Symp. Ser. 544 (1994). Silk proteins modified by genetic engineering are capable of displaying new features alongside the native properties. Wong et al., 54 Adv. Drug Deliv. Rev. 1131 (2002); Cappello et al., 3 Biotechnol. Prog. 198 (1990); Megeed et al., 54 Adv. Drug Deliv. Rev. 1075 (2002). Other examples of bioengineered silks can be described, from inclusion of molecular triggers to control of self-assembly (Szela et al., 1 Biomacromol. 534 (2000); Winkler et al., 39 Biochem. 12739 (2000)), chimeric silk proteins for controlled mineralization (Wong et al., 103 P.N.A.S. 9428 (2006); Huang et al., 28 Biomats. 2358 (2007)), and recent all silk block copolymer designs. Rabotyagova et al., 10 Biomacromol. 229-36 (2009).

Thus, "silk fibroin" includes silkworm fibroin and insect or spider silk protein. Lucas et al., 13 Adv. Protein Chem. 107 (1958). For example, fibroin is obtained from a solution containing a dissolved silkworm silk or spider silk. The silkworm silk protein is obtained, for example, from *Bombyx mori*, and the spider silk is obtained from *Nephil clavipes*. There are many different silks, however, including spider silk (e.g., obtained from *N. clavipes*), transgenic silks, genetically engineered silks, such as silks from bacteria, yeast, mammalian cells, transgenic animals, or transgenic plants (see, e.g., WO 97/08315; U.S. Pat. No. 5,245,012), and variants thereof, that may be used.

An aqueous silk fibroin solution may be prepared from silkworm cocoons using techniques known in the art. Suitable processes for preparing silk fibroin solution are disclosed, for example, in U.S. patent application Ser. No. 11/247,358; WO/2005/012606; WO 08/127,401. For example, *B. mori* cocoons are boiled for about 30 minutes in an aqueous solution. The aqueous solution may be 0.02 M sodium carbonate. The cocoons are rinsed with water to extract the sericin proteins and the extracted silk is dissolved in an aqueous salt solution. Salts useful for this purpose include, but not limited to, lithium bromide, lithium thiocyanate, calcium nitrate or other chemicals capable of solubilizing silk. For example, the extracted silk maybe dissolved in about 9M to 12 M LiBr solution at 60° C. for 4 hours, yielding a 20% (w/v) solution. The salt is consequently removed using dialysis. The solution maybe centrifuged to remove small amounts of silk aggregates that may form during the process, usually from environment contaminants that are present on the cocoons. The final concentration of silk fibroin aqueous solution may be approximately 8% (w/v). To obtain a silk fibroin solution with a higher concentration, the silk fibroin solution with a lower concentration may be dialyzed against a hygroscopic polymer, for example, PEG, a polyethylene oxide, amylose or sericin. For example, an 8% silk fibroin solution may be dialyzed against 10% (w/v) PEG (10,000 g/mol) solution. The dialysis is for a time period sufficient to result in a final concentration of aqueous silk solution between 10% to 30%. In most cases dialysis for 2 to 12 hours is sufficient.

The secondary structure of silk fibroin generally determines the solubility and biodegradability of the material. α-helix and random coil structures enhance solubility of silk fibroin in aqueous solutions, whereas β-sheet structures prevent silk protein from dissolving in aqueous solutions. Huemmerich et al., 43 Biochem. 13604 (2004). In addition, the degradation rate of silk fibroin increases with decreased β-sheet content. Li et al., 24 Biomats. 357 (2003). β-sheet crystalline structure of silk protein can be induced by methods known to one skilled in the art, such as methanol treatment, water annealing treatment, lowering pH, applying electric field, applying shearing force, and the like.

The silk fibroin solution can be combined with one or more biocompatible polymers such as polyethylene oxide, polyethylene glycol, collagen, fibronectin, keratin, polyaspartic acid, polylysin, alginate, chitosan, chitin, hyaluronic acid, and the like; or one or more active agents, such as cells, enzymes, proteins, nucleic acids, antibodies and the like, as described herein. See, e.g., WO 04/062697; WO 05/012606. Silk fibroin can also be chemically modified with active agents in the solution, for example through diazonium or carbodiimide coupling reactions, avidin-biodin interaction, or gene modification and the like, to alter the physical properties and functionalities of the silk protein. See, e.g., PCT/US09/64673; U.S. Application Ser. No. 61/224,618; Ser. No. 12/192,588.

Silk fibroin can be coupled with various biomolecules, via carbodiimide-mediated reactions. For example, bone morphogenetic protein 2 (BMP-2) could be coupled to silk fibroin to induce bone formation (Karageorgiou et al., 71 J. Biomed. Mater. Res. A 528 (2004)); RGD peptide could be coupled to silk fibroin to promote cell attachment. Karageorgiou et al., 2004. Surface modification of silk fibroin scaffold with active agents such as enzymes or cytokines through carbodiimide-mediated reactions to form gradient of the active agents within the scaffold have also been reported. See, e.g., U.S. Patent Pub. No. 2007/0212730. Direct covalent coupling may negatively impact the bioactivity of particular biomolecules, however, because of reactions at amine groups. The present invention thus provides for an alternative approach by linking avidin or biotin to silk, and then linking other active agents (e.g., proteins or drugs) to the silk via silk-avidin-biotin-drug or silk-biotin-avidin-biotin-drug bridges. Because avidin and its derivatives, such as streptavidin, are natural homotetramers containing four biotin binding sites, the avidin-biotin linkages between silk and active agents not only reduce the potential activity loss of bioactive molecules, but also increase the number of bound biomolecules.

The present invention provides for the coupling strategies of linking silk fibroin to biomolecules through avidin-biotin interaction, thus expanding the area of functionalization of silk-based protein biomaterials.

In one embodiment, silk protein was covalently coupled with NeutrAvidin to reduce non-specific binding while maintaining affinity to biotin, via 1-ethyl-3-(3-dimethylaminopropyl)-carbodiimide (EDC) coupling. Subsequently, bioactive molecules were linked to the silk protein via avidin-biotin interactions. NeutrAvidin was coupled either to the bulk silk fibroin protein molecules in aqueous solution or to the surface of silk particles. The binding stoichiometry of NeutrAvidin to silk spheres was evaluated. Using this coupling strategy, anti-CD3 monoclonal antibody was successfully coupled to the surface of silk microspheres via NeutrAvidin/biotin interaction, and the functionalized microspheres exhibited specific binding to the CD3$^+$ Jurkat T-cell line. In other embodiments, biotinylated antibodies were covalently coupled to silk films and diazo-silk films via NeutrAvidin/biotin interaction.

The embodiments of the present invention provide for methods of functionalizing a silk fibroin protein in an aqueous solution with a bioactive agent, comprising the steps of reacting a silk fibroin protein molecule with avidin in an aqueous solution to form a silk fibroin protein-avidin conjugate, wherein avidin is linked to the silk fibroin protein through a covalent bond; providing a biotinylated bioactive agent; and contacting the silk fibroin protein-avidin conjugate with the biotinylated bioactive agent in an aqueous solution to form a silk fibroin protein-avidin-biotin-bioactive agent conjugate, wherein the biotinylated bioactive agent is linked to the silk fibroin protein-avidin conjugate through avidin-biotin interaction.

Alternatively, the method may also comprise reacting a silk fibroin protein molecule with biotin in an aqueous solution to form a silk fibroin protein-biotin conjugate, wherein biotin is linked to the silk fibroin protein through a covalent bond; providing an avidin-biotinylated active agent formed by linking avidin to a biotinylated active agent; and contacting the silk fibroin protein-biotin conjugate with the avidin-biotinylated active agent in an aqueous solution to form a silk fibroin protein-biotin-avidin-biotin-active agent conjugate, wherein the avidin-biotinylated active agent is linked to the silk fibroin protein-biotin conjugate through avidin-biotin interactions.

In some embodiments of the present invention, avidin can be linked to the silk fibroin protein molecules via a carbodiimide coupling reaction using 1-Ethyl-3-(3-dimethylaminopropyl)-carbodiimide (EDC). The carbodiimide-mediated coupling procedure was similar to that described in the literature with some modifications. Chen et al., 67 J. Biomed. Mater. Res. A 559-70 (2003).

In some embodiments, NeutrAvidin can be added to the reactive silk fibroin solution, and the silk allowed to self-assemble into a water-insoluble film. The time the solution is allowed to self-assemble can be used to control the nature of the film. For example, when the reaction lasted for 5 hours at room temperature, all of the silk formed into film; when the reaction time was reduced to 2.5 hours, approximately half of the silk formed such structures, as estimated by weighing the film. A reaction time of 30 minutes could eliminate this silk film formation process during the bulk solution reactions. After the reaction, the solution containing silk fibroin protein-NeutrAvidin conjugate was dialyzed against water to remove unreacted compounds. The dialysis time was chosen to avoid silk self-assembly into aggregates; for example, 5 hours of dialysis may be used.

Due to the high affinity of avidin for biotin ($K_D=10^{-15}$ M), biotinylated molecules can be rapidly coupled to the silk-avidin conjugate under mild conditions (neutral pH, room temperature) in a short time range. Vast variety of biotinylated active agents may be used. The active agents of the present invention can be any active agent that can be biotinylated as known by one skilled in the art.

The embodiments of the present invention also provide for silk fibroin proteins that are functionalized with a bioactive agent in bulk solution, prepared through the functionlization methods of the present invention, as discussed herein. The functionalized silk fibroin protein solution may be further fabricated into variety of silk material formats, such as a gel, hydrogel, film, diazo-film, sponge, or porous scaffold. Fabrication of these materials does not require organic solvents, hence is more suitable for therapeutic applications.

The present invention thus provides for a bioactive agent functionalized silk material in a variety of formats, such as a hydrogel, film, porous sponge scaffold, comprising silk fibroin protein molecules functionalized with a bioactive agent. The silk material of the invention is prepared from the silk fibroin solution. The bulk silk fibroin protein molecules in the silk fibroin solution are linked to bioactive agent through avidine-biotin linkage. Functionalization of silk fibroin protein with bioactive agents may through either a silk fibroin protein-avidin-biotin-bioactive agent conjugate or a silk fibroin protein-biotin-avidin-biotin-bioactive agent conjugate, as described in the functionalization method of the present invention.

In a particular embodiment, the NeutrAvidin-conjugated silk fibroin protein solution was further processed into hydrogel by sonication treatment. NeutrAvidin conjugated silk protein can require a longer time for gellation, compared with unconjugated silk protein, with the same amount of sonication energy input. This may due to the interaction of NeutrAvidin with the hydrophobic domains of silk protein molecules, thus inhibiting the formation of silk crystalline β-sheet structure. Wang et al., 2008. When using a longer sonication time (e.g., 60 seconds), unconjugated silk can gel almost immediately after sonication, while the NeutrAvidin-conjugated silk may form white inhomogeneous aggregates (Table 1):

TABLE 1

Sonication-induced NeutrAvidin-silk gelation

| | Gelation time (mins) | |
|---|---|---|
| Sonication time (secs) | Unconjugated silk | NeutrAvidin-conjugated silk |
| 15 | 40 | >60 |
| 30 | 10 | 15 |
| 60 | 1 | aggregate |

Figure 5:
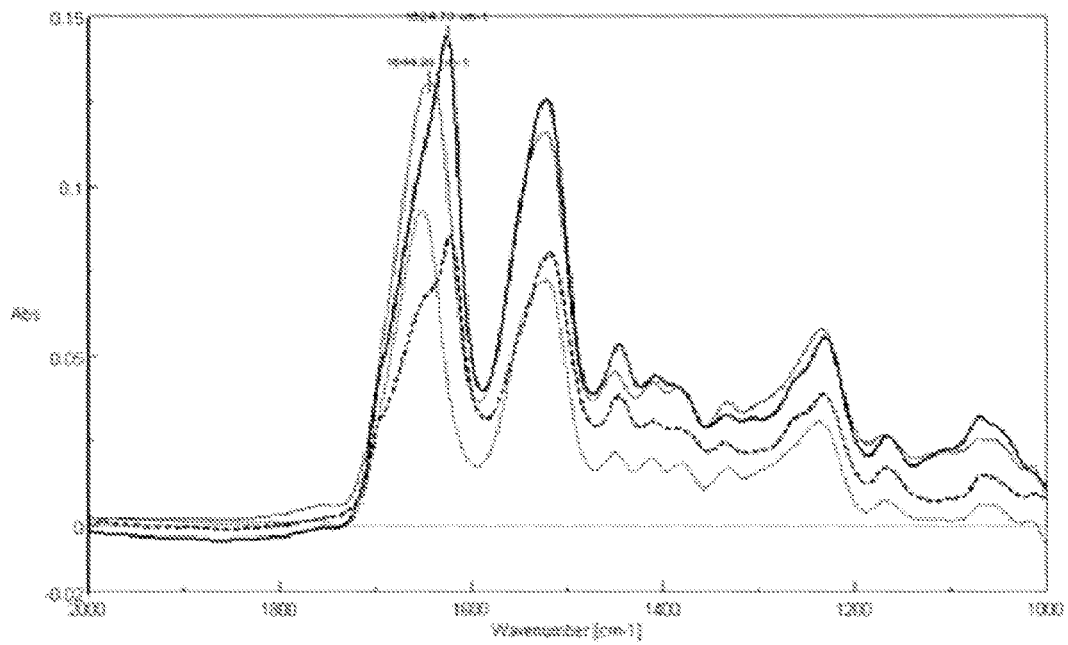
FIG. 5 shows FTIR spectra of NeutrAvidin-silk before and after gelation. Lyophilized NeutrAvidin-silk solution and corresponding gel (2% (w/v)) were used for the measurement. The same concentration of unmodified silk solution and gel served as control. Thick solid line: NeutrAvidin-silk gel. Thin solid line: NeutrAvidin-silk solution. Thick dotted line: silk gel. Thin dotted line: silk solution.

The structure of NeutrAvidin-silk gel formed was characterized with FTIR, using an unmodified silk gel as control. Similar to unmodified silk, NeutrAvidin-silk underwent a similar structural transition from random coil (band at 1645 cm$^{-1}$) to β-sheet (band at 1625 cm$^{-1}$) structure upon sonication, indicating the formation of Silk II structure in the gel (FIG. 5). For both silk and NeutrAvidin-silk, different gelation times resulted in the formation of the same β-sheet structure with a characteristic band at about 1625 cm$^{-1}$.

The amount of NeutrAvidin in silk gel was then determined using fluorescently labeled biotin, Atto 610-Biotin. Silk gels with various volumes were incubated in an Atto 610-Biotin solution with a constant volume and concentration. After washing the gels by centrifugation, the amount of bound Atto 610-Biotin was determined by measuring UV absorbance of the supernatants and comparing with the original amount added. Non-specific binding of Atto 610-Biotin to plain silk gel without NeutrAvidin coupling was also measured, and the result (approximately 10% of the specific binding) was subtracted from the data reported. As shown in FIG. 1 (top panel), the molar ratio between bound Atto 610-Biotin and silk increased with the increase of silk concentration in the gel, reaching the maximal level of approximately 4.5 at a silk concentration of 0.6 µM. The molar ratio, however, decreased when the silk concentration was higher than 0.6 µM, suggesting that the Atto 610-Biotin in solution was not adequate to maintain the binding equilibrium. The result was confirmed by another experiment in which the amount of NeutrAvidin silk gel was kept constant while the concentration of Atto 610 biotin added was varied. It was found that the number of Atto 610-Biotin molecules bound to silk increased and reached the maximal level of about 5.5 when the Atto 610-Biotin concentration in solution was above 60 µM (FIG. 1, bottom panel).

Because the two experiments were performed separately using different preparations of NeutraAvidin-silk, the differences in stoichiometry may reflect statistical deviations due to the carbodiimide reaction. NeutraAvidin is a homotetramer that has four biotin binding sites, so the results suggested that one silk molecule was associated with more than one NeutrAvidin, assuming NeutrAvidin molecules were evenly distributed among silk fibroin molecules. Because the original amount of NeutrAvidin used was about three-times that of silk (see Examples, herein), the efficiency of the coupling reaction was therefore 30% to 40%.

Figure 6:
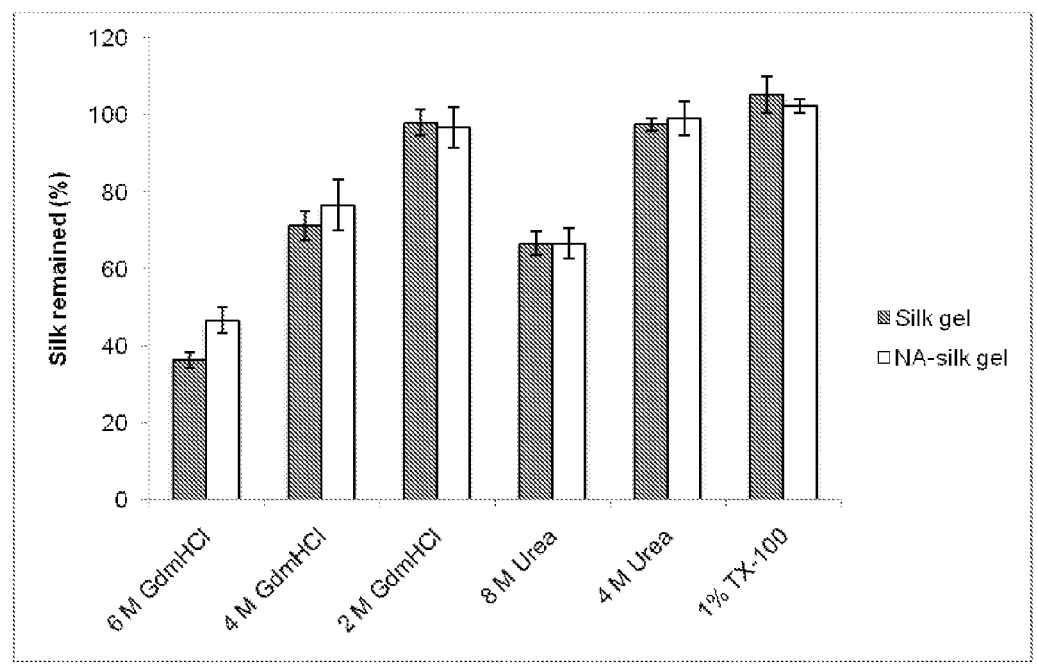
FIG. 6 presents data on the chemical stability of NeutrAvidin-silk gel. Lyophilized NeutrAvidin-silk gel (2% (w/v)) and silk gel (control) were immersed in various chemical solutions. The remaining mass after 3 days incubation was determined and compared with the original mass. Gray columns: NeutrAvidin-silk gel (NA-silk gel). White columns: silk gel.

Silk gels consist of extensive polymer chain networks formed by intermolecular physical crosslinking between silk crystalline β-sheets, therefore, presenting remarkable chemical and physical stabilities. Matsumoto et al., 110 Phys. Chem. B 21630 (2006). The loss of mass of silk and NeutrAvidin-silk gel was checked using different chemical denaturants, i.e., guanidium hydrochloride (GdmCl), urea and Triton X-100. Both gels were stable with no loss of mass in up to 2 M GdmHCl, up to 4 M urea and 1% Triton X-100 (FIG. 6). Approximately 20% and 50% to 60% mass loss was found if the concentration of GdmCL was increased to 4 M and 6 M, respectively, and 30% mass loss was found if the urea concentration was increased to 8 M urea. Both silk and NeutrAvidin-silk gels were more susceptible to GdmCl when compared to other chemicals, consistent with the observation from previous studies using silk microspheres. Lammel et al., 31 Biomats. 4583 (2010). Highly stable NeutrAvidin-silk gels will be useful in applications that require gel stability for a long period of time to enable sustained release of bioactive molecules.

Figure 2:
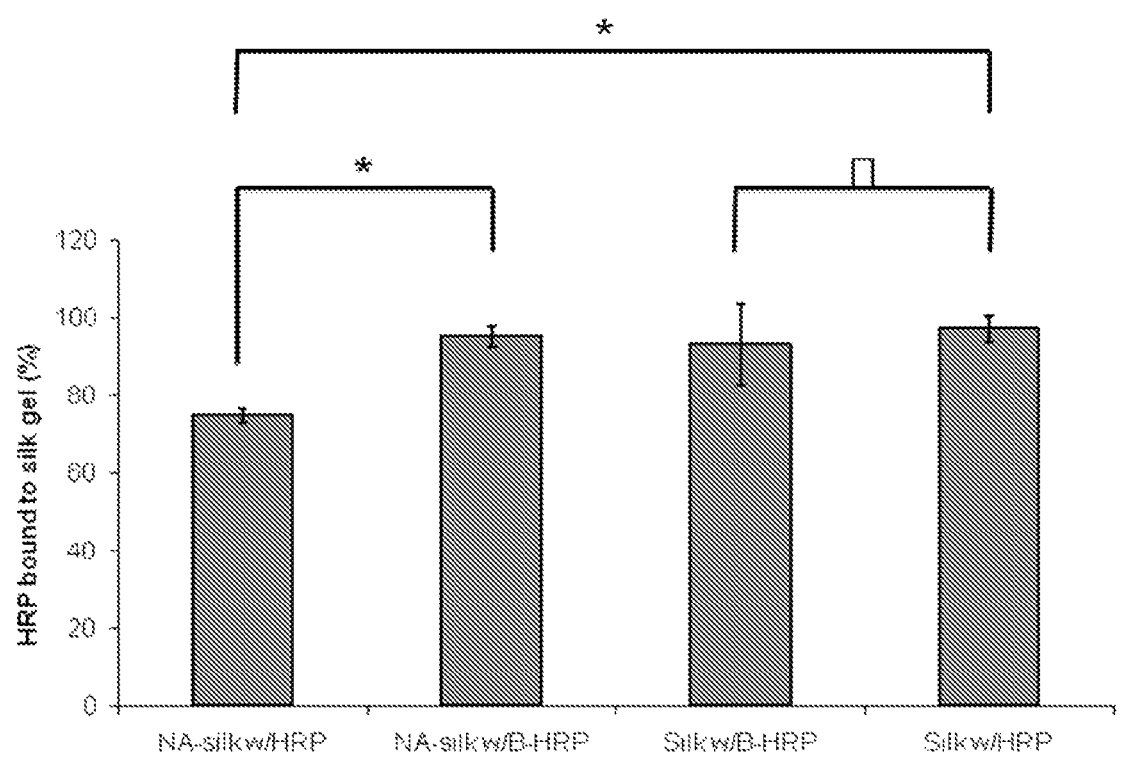
FIG. 2 depicts the binding profile of horse radish peroxidase (HRP) to silk fibroin protein via biotin-NeutrAvidin linkage (Strep Silk w/B-HRP). Biotin-HRP was mixed with NeutrAvidin-coupled silk fibroin solution and the gelation of mixed solution was induced by sonication. The amount of biotin-HRP bound to silk fibroin protein in the silk gel was determined by measuring the activity of HRP and then comparing with the activity of the original amount of HRP before the reaction. Non-biotinylated HRP (Strep Silk w/HRP) and non-NeutrAvidin-coupled silk (Silk w/B-HRP Silk w/HRP) were used as controls. Data are shown as means±standard deviation (n=4). Asterisk (*) indicates significant difference ($p \leq 0.05$) between samples. Cross (x) indicates no significant difference ($p > 0.05$) between samples. NA=NeutrAvidin; B-HRP=biotin-HRP.

In one embodiment of the present invention, Biotinylated HRP was employed to demonstrate the specific binding of biotinylated protein to NeutrAvidin-silk. As shown in FIG. 2 when non-biotinylated HRP was used as a control, ~70% of HRP bound to NeutrAvidin-silk (NA-Silk w/HRP) and could not be washed away, indicating that there was non-specific binding of HRP to silk. When biotinylated HRP was used, ~90% of biotinylated HRP bound to NeutrAvidin-silk (NA-Silk w/B-HRP), significantly higher than the non-specific binding of HRP ($p<0.01$). The results demonstrated that the NeutrAvidin-biotin interaction facilitated specific binding of the target protein molecules to silk matrices. Interestingly, when using unconjugated silk as control experiments (non-NeutrAvidin coupled), both biotinylated HRP and non-biotinylated HRP exhibited non-specific binding (~90%) to silk (FIG. 2). Comparing the binding of non-biotinylated HRP (~70%) with NeutrAvidin-silk and with unconjugated silk (~90%), the binding of HRP to silk non-specifically may partially be attributed to the carboxylic groups on silk molecules, or the charge effect. Other effects, such as hydrophobic interactions, might also contribute to the non-specific binding.

Non-specific binding may significantly influence the protein bioactivity due to the distortion of the protein structure, though this may not seem to be the case for HRP. In addition, if the bound protein molecules are receptors or cytokines that need to exhibit specific docking sites to their ligands, non-specific binding may largely decrease the binding efficiency due to the steric hindrance of binding sites. Thus, non-specific binding can be minimized for many applications. To reduce non-specific binding and increase the binding sensitivity, other functionalization strategy may be used, such as forming a conjugate of biotinylated silk-streptavidin-biotinylated bioactive agent. The biotinylated silk fibroin may be obtained by carbodiimide-mediated crosslinking reaction between carboxylic groups in silk and biotin hydrazide. Streptavidin or premixed streptavidin-biotinylated functional groups can be incorporated subsequently. Diamandis et al., 1991. On the other hand, non-specific binding might be useful in some applications, such as sustained drug delivery, in order to increase drug loading and decrease drug release rate.

The present invention thus provides for functionalization strategies of silk biomaterials using a universal coupling strategy based on streptavidin(avidin)-biotin interaction. The material modification based on streptavidin (avidin)-biotin interaction has been used in tissue engineering to incorporate functional groups, such as integrin-binding peptide RGD and a variety of growth factors, in a biopolymer matrix, e.g., collage and polyacrylamide hydrogel, in order to promote cell attachment, growth and differentiation. Boyce et al., 1993; Burnham et al., 2006; Chen et al., 2000; Clapper et al., 2008; Hynd et al., 2007a; Hynd et al., 2007b. Current functionlization techniques, however, are mainly surface-functionalization of the polymerized material. For example, the active agent is usually biotinylated via chemically coupling relation reactions or blended with a biotinylated copolymer (e.g., biotinylated PEG) during the material processing; and only subsequently the streptavidin-coupled functional groups or the streptavidin-biotinylated functional groups are introduced, in most of the cases to the surface of the polymerized material by simply immersing the material in the solution containing the functional group.

Incorporation of functional groups within a bulk material, such as within a hydrogel, is superior to the surface functionalization in many applications such as cartilage and soft tissue engineering, as the encapsulated cells can grow and differentiate in a sustained and homogeneous manner under the support of surrounding high-density functional groups from three dimensions. Incorporation of functional groups in the bulk material was difficult to achieve, before the present invention, however, either because the harsh conditions used to crosslink polymer chains were usually detrimental to the streptavidin (avidin, or other avidin derivatives) as well as functional groups, or because the addition of functional groups would influence the polymer crosslinking.

The present invention thus provides for a unique and different coupling strategy in producing functionalized silk hydrogel: streptavidin moiety was actively coupled to silk fibroin protein via carbodiimide-mediated crosslinking reaction, and the biotinylated functional group was subsequently incorporated into silk in bulk solution via streptavidin-biotin interaction, prior to gelation. Further, a short ultrasonication (e.g., ~30 second) to induce silk gelation was not detrimental to the bioactive molecules incorporated, such as growth factors. Wang et al., 2008. The incorporation of functional groups within a bulk gel material will be superior to the surface functionalization in many applications such as cartilage and soft tissue engineering, as the encapsulated cells can grow and differentiate in a sustained and homogeneous manner under the support of surrounding high-density functional groups from three dimensions. The technique can also be used to functionalize silk materials other than hydrogels, for example, films or porous sponge scaffolds, as the fabrication of these materials does not require organic solvents and, therefore, is intimate to the functional groups incorporated.

The embodiments of the present invention also provide for a method of functionalizing the surface of a silk particle with a bioactive agent comprising providing a silk particle; providing a biotinylated active agent; reacting the silk particle with avidin in an aqueous solution to form a silk particle-avidin conjugate, wherein avidin is linked to the silk particle through a covalent bond; contacting the silk particle-avidin conjugate with the biotinylated active agent to form a silk particle-avidin-biotin-active agent conjugate, wherein the biotinylated active agent is thus linked to the silk particle-avidin conjugate through avidin-biotin interaction.

Alternatively, the "docking" strategy can be modified using biotinylated silk-streptavidin-biotinylated functional group. For example, biotinylated silk fibroin can be obtained by carbodiimide-mediated crosslinking reaction between carboxylic groups in silk and biotin hydrazide. Streptavidin or premixed streptavidin-biotinylated functional groups can be incorporated subsequently. Diamandis & Christopolous, 37 Clin. Chem. 625 (1991); Vernette et al., 2003.

Silk particles of the present invention may be silk fibroin microspheres or nanospheres prepared by the methods known by one skilled in the art. For example, silk microspheres may be prepared by using liposomes as templates and freeze-thawing the mixture of silk fibroin and lipid. See, e.g., WO 08/118,133. Depending on the applications of the silk materials, microspheres with a size (e.g., diameter) ranging from 1 μm to 1000 μm, inclusive, can be used. Silk fibroin nanoparticles with size ranging from 1 nm to 1000 nm, inclusive, can also be used in the present invention, for example to more specifically localize the drug delivery in tumors or to achieve more active cellular uptake. Silk nanospheres may be prepared by the methods known by one skilled in the art, for example, using method described in the literature. See, Zhang et al., 9 J. Nanoparticle Res. 885 (2007).

Thus, in embodiments, avidin, or its derivatives (e.g., NeutrAvidin, streptavidin, or CaptAvidin) can be covalently conjugated to silk particles. In one embodiment, avidin can be linked to the silk particles via a carbodiimide coupling reaction using 1-ethyl-3-(3-dimethylaminopropyl)-carbodiimide (EDC). The reaction conditions are similar as discussed above for the coupling reactions of avidin and silk fibroin protein in solution.

In a particular embodiment, NeutrAvidin was conjugated to the surface of silk microspheres via EDC coupling reaction. The size and morphology of microspheres was not changed by the reaction. The microspheres after the reaction remained their original size (2 μm to 3 μm) and porous surface morphology, as previously reported. Wang et al., 2007. HRP-conjugated NeutrAvidin was used in the coupling reaction to quantify the NeutrAvidin bound to silk microspheres. The stoichiometry of the reaction was in the range of 1 μg to 3 μg NeutrAvidin per 1 mg silk fibroin, which corresponds to a molar ratio of about 1:150.

Figure 3:
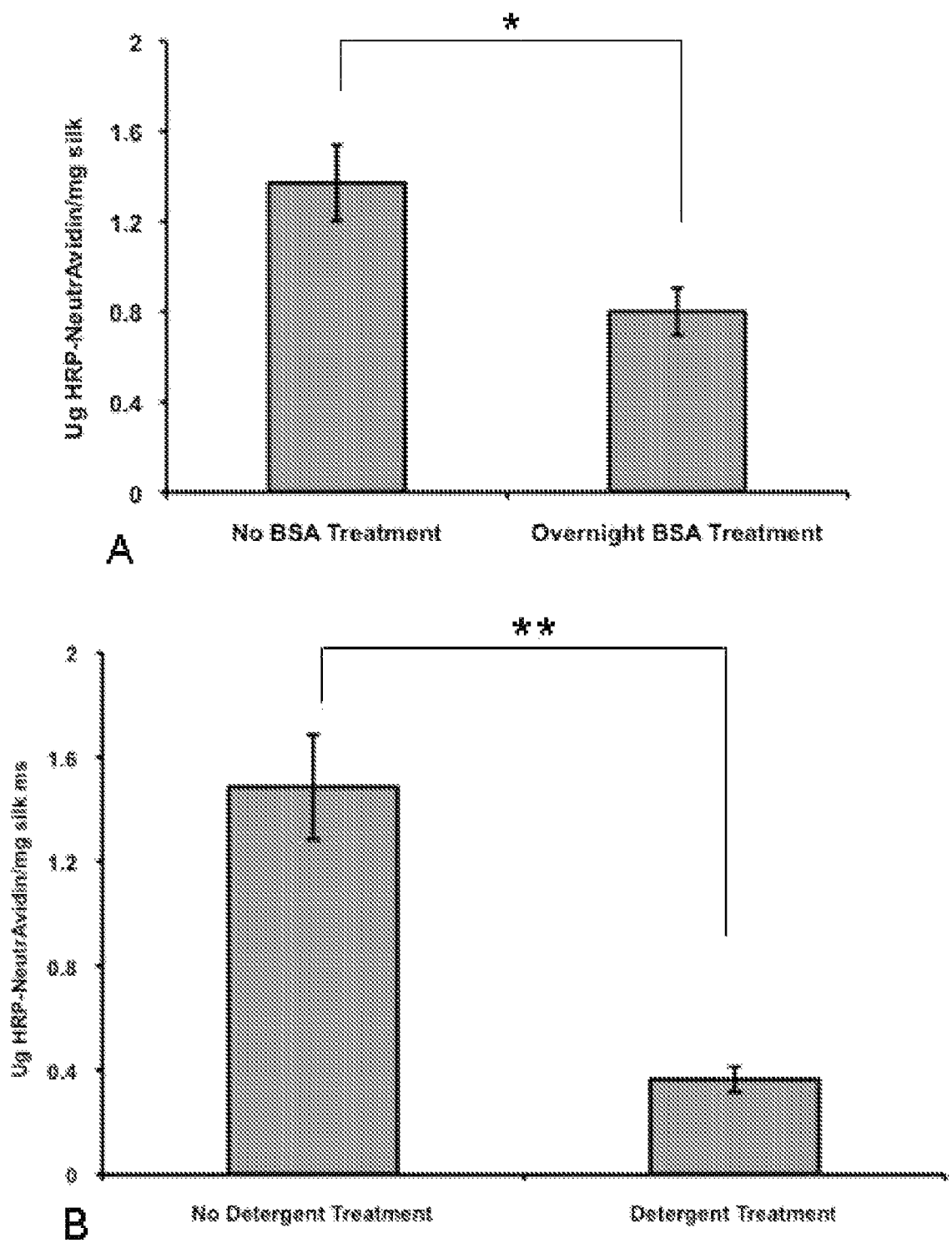
FIGS. 3A and 3B show a reduction of non-specific binding of HRP-NeutrAvidin on silk microspheres.

Different methods can be used to reduce non-specific binding of NeutrAvidin to silk microspheres. For example, to reduce non-specific binding of NeutrAvidin, silk microspheres were treated with BSA prior to the coupling reaction. It was found that the BSA treatment reduced approximately 40% of the NeutrAvidin binding as compared to that without BSA treatment ($p<0.05$, FIG. 3A). Treatment with Triton X-100 after the addition of NeutrAvidin also significantly reduced the amount of HRP-conjugated NeutrAvidin on the microspheres by 75% ($p<0.01$, FIG. 3B). Triton X-100 treatment, however, caused loss of silk microspheres (up to 30 wt %), probably due to the decomposition of some silk microspheres containing higher content of residual phospholipids that are susceptible to detergents.

In particular, when using the HRP-conjugated NeutrAvidin to couple NeutrAvidin to silk microspheres, the contribution of HRP to the non-specific binding may be considered, although this binding can be reduced by treatment with BSA or detergent. HRP may contribute to the non-specific binding of HRP-conjugated NeutrAvidin to microspheres, perhaps because of electrostatic and hydrophobic interactions between HRP and silk. Compared to HRP, non-specific binding of NeutrAvidin to silk may not be as significant, because the efficiency of EDC coupling of NeutrAvidin to the bulk silk fibroin protein molecules may be as low as 30%.

Figure 7:
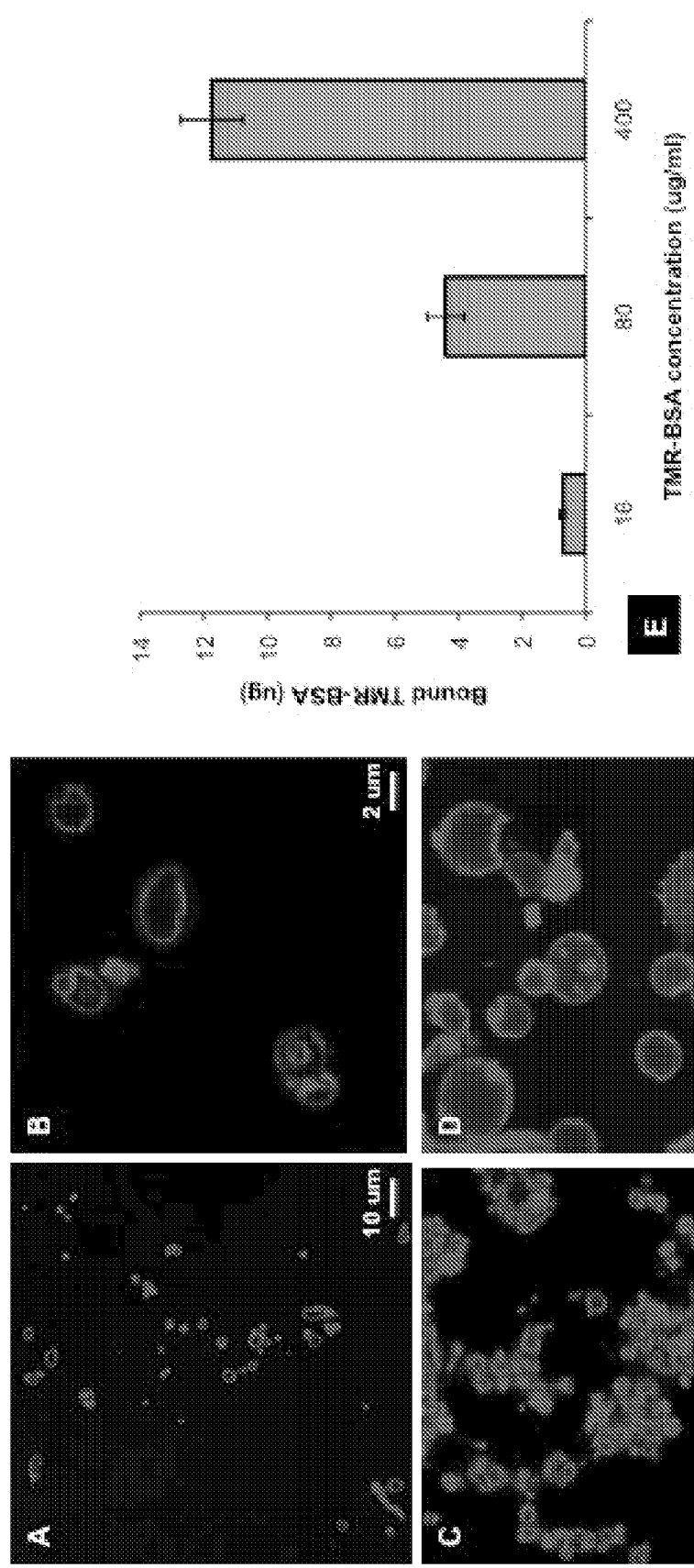
FIG. 7 shows determination of non-specific binding of TMR-BSA on silk microspheres. Binding of TMR-BSA on the surface of silk microspheres was fluorescently detected by confocal laser scanning microscope.

Fluorescent TMR-BSA was used to further investigate the non-specific binding of BSA to silk microspheres. Upon incubating TMR-BSA with silk microspheres, confocal images showed a red layer of TMR-BSA on the surface of the microspheres that could not be removed with water (FIGS. 7A-7D). Further quantitative analysis showed that the binding of TMR-BSA to silk microspheres was concentration dependent (FIG. 7E). Approximately 12 μg TMR-BSA bound to 10 mg silk microspheres when the TMR-BSA concentration was 400 μg/ml, above which the fluorescence in the supernatants was too high for accurate measurement (FIG. 7E). The experiment confirmed the non-specific binding of BSA to silk microspheres and, therefore, its use to pre-treat the spheres and improve the specific coupling of NeutrAvidin.

These data suggested that HRP-coupled NeutrAvidin may also bind non-specifically to silk microspheres, though this binding can be reduced by treatment with BSA or detergent. As discussed herein, non-specific binding might be attributed to both electrostatic and hydrophobic interactions between HRP and silk. Compared to HRP, non-specific binding of NeutrAvidin to silk might be insignificant, as the efficiency for EDC coupling of NeutrAvidin to silk was only 30%. Overall, BSA treatment seems to be the best way to reduce non-specific binding without losing labeled material. Strong non-specific binding to silk was also observed for other proteins, such as antibodies. Therefore, the BSA treatment can be useful in the other applications using silk fibroin.

Further, non-specific binding to silk was observed for proteins other than HRP, such as antibodies. Because the BSA treatment appeared to reduce the non-specific binding without loss of silk materials, it may serve as a useful treatment for functionalization of silk materials with various bioactive agents.

Moreover, to minimize non-specific binding to silk particles, functionalization strategies such as those described for silk hydrogel may also be used. For example, instead of direct streptavidin coupling, biotin may be coupled to the surface of silk microspheres and streptavidin-biotinylated functional group may be added subsequently, thus forming a conjugate of biotinylated silk particles-streptavidin-biotinylated bioactive agent.

Figure 4:
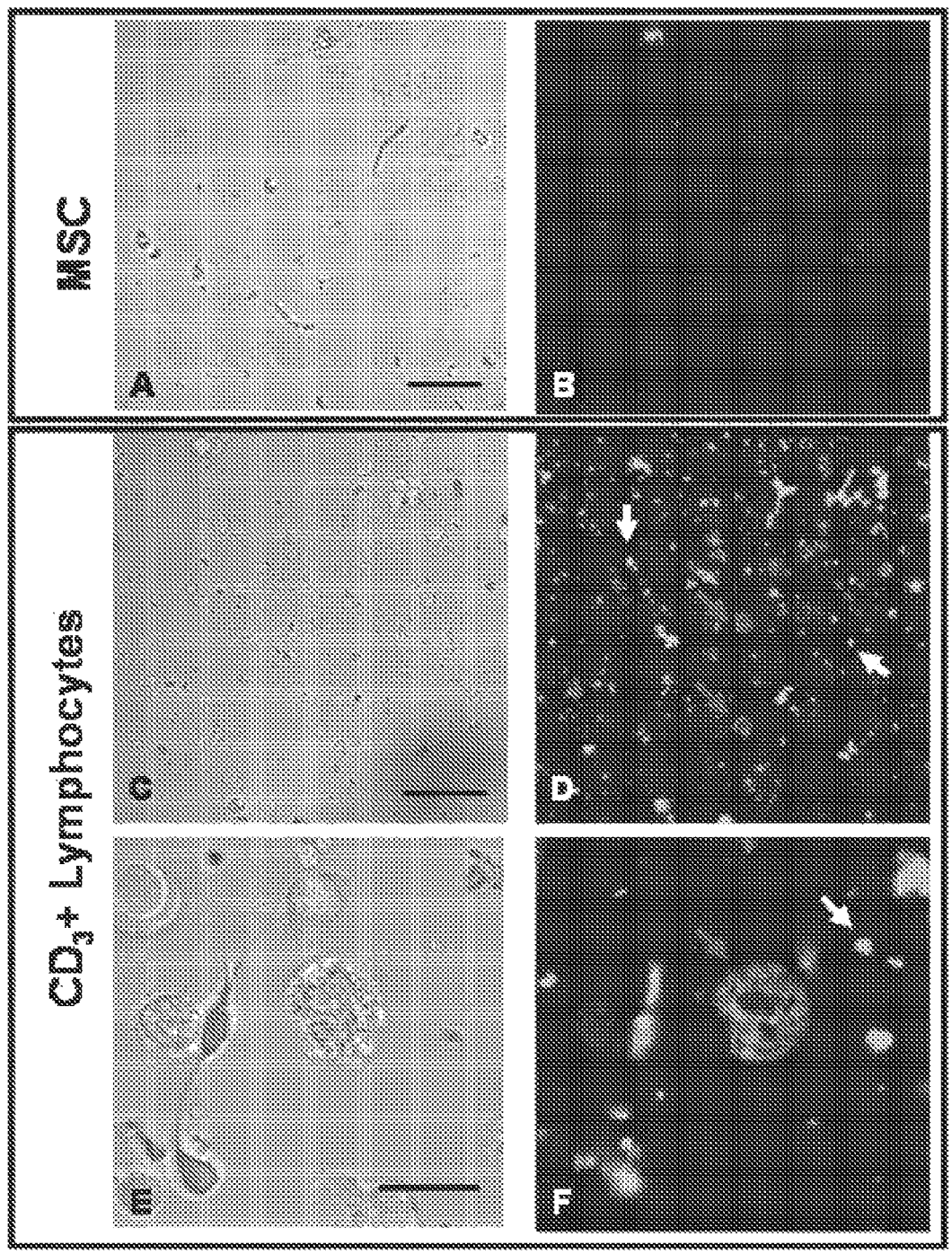
FIG. 4 is a series of photographs depicting the linkage of biotinylated anti-CD3 antibody to the surface of silk microspheres coupled with NeutrAvidin, and the specific targeting of the silk microspheres to CD3$^+$ T-cell line Jurkat.

In a particular embodiment, Biotinylated anti-CD3 antibody was linked to NeutrAvidin-coupled silk microspheres, and the binding and internalization of the microspheres with the CD3-positive T-lymphocytic cell line Jurkat was demonstrated by confocal laser scanning microscope. FITC-labeled NeutrAvidin was used in the reaction and the resulting green fluorescent silk microspheres were monitored in some cells (FIG. 4). The cells with bound and internalized microspheres had a different appearance from the free cells. The use of trypan blue staining indicated that cells were alive before adding silk microspheres. This rules out the possibility that some cells were dead before adding microspheres and thus that the microspheres could enter the dead cells more easily.

Nanoparticles (less than 1 µm, less than 100 nm), especially those with lipophilic properties, readily across the cell lipid bilayer membrane and enter the cell cytoplasm. In some cases, these nanoparticles cause cell death or apoptosis. Harush-Frenkel et al., 25 Crit. Rev. Ther. Drug Carrier Sys. 485-544 (2008). Phagocytosis of microparticles, including silk microparticles, has been described in the literature. Panilaitis et al., 24 Biomats. 3079-85 (2003). Little literature describes microparticle internalization in cells other than macrophages. Among these, the internalization of polystyrene microspheres in different cell lines has been reported, and such internalization was highly dependent on particle size and concentration; Only those particles sized below 2 µm could be internalized, though the level was much lower than those with nanometer-size (500 nm). Bradley et al., 18 J. Fluoresc. 733-39 (2008). The microspheres were assumed to be internalized via endocytosis. Silk particle internalization may influence cell growth and activity. Additionally, for the interaction between silk and cells, the size and concentration of silk microspheres may affect the cell internalization. Silk spheres may vary in size from nanometers to micrometers. Different cell types may also internalize silk particles in different ways, or fail to internalize them altogether. For example, silk microspheres were not internalized by human bone marrow-derived mesenchymal stem cells. Recently, a new method of preparing silk nanoparticles with sizes of 300 nm to 400 nm has been reported. Wang et al., 31 Biomats. 1025 (2010). The one-step preparation method does not require organic solvent or high temperature and, therefore, would be suitable as a targeting vehicle after surface modification using the strategies described herein.

The embodiments of the present invention thus provide for functionalizing silk materials, e.g., hydrogel and microspheres, based on the interaction between biotin and streptavidin (or avidin and its derivatives). Briefly, silk fibroin in solution may be covalently coupled with avidin, and may be further induced to form gel by sonication; the surface of silk microspheres may be covalently coupled with avidin without influencing the microsphere morphology. The coupling reactions retained the self-assembly features of the silk fibroin protein. Biotinylated bioactive agents could be incorporated in the modified silk hydrogel and on the surface of silk particles via avidin-biotin interaction. For example, fluorescently labeled biotin may be linked to silk hydrogel and the surface of microspheres, although non-specific binding was also observed in both cases. Using fluorescently labeled biotin (e.g., Atto 610-Biotin), a stoichiometry of bound avidin (biotin) to silk fibroin could be determined. As an example, molar ratio of silk:biotin was determined to be 1:4, indicating one silk molecule was associated with one NeutrAvidin molecule, assuming NeutrAvidin molecules were evenly distributed among silk molecules.

Non-specific binding of NeutrAvidin to silk microspheres was also observed. Pretreatment of silk microspheres with BSA or post-treatment with detergent (e.g., Triton-X 100) reduces nonspecific binding. In one embodiment, biotinylated anti-CD3 antibody was coupled to the surface of NeutrAvidin-conjugated silk microspheres. Functionalized silk microspheres then specifically bound $CD3^+$ Jurkat T-cells. The attachment and internalization of silk microspheres to the T-cells was characterized by confocal laser scanning microscope using the FTIC-labeled NeutrAvidin as the coupling agent.

In the represent invention, an avidin-modified silk was used as a biomaterial platform for functionalization with a variety of biotin-linked active agents, such as antibodies and growth factors, to expand functional materials space. The present invention thus provides for a new tool of functionalizing a variety of silk biomaterials via highly-specific interaction between streptavidin and biotin. This functionalization strategy is easy, fast, and universally feasible, thus may be useful in many biomedical applications.

In general, active agents that may be biotinylated and attached to silk-avidin conjugate include, but are not limited to, cell binding domains, cell signaling factors, proteins, antibodies or portions or fragments thereof, peptides, nucleic acids, peptide nucleic acid, aptamers, antigens or epitopes, hormones, hormone antagonists, growth factors, cytokines, cytotoxins, enzymes, antimicrobial compounds, anti-inflammatory agents, immuno-suppressive agents, chemotherapeutic drugs or agents, steroids, antibiotics, analgesics and analgesic combinations, dyes, small molecules, and combinations thereof. Thus, one embodiment, the functionalized silk biomaterial of the present invention contains at least one active agent.

In addition to the functionalized silks described herein, the present invention provides for combining the functionalized silk with other silk-based biomaterials that comprise active agents or cells. Exemplary active agents include antibodies such as anti-CD3 antibody, chemotherapeutic agents (e.g., anticancer agents), cell attachment mediators, such as the peptide containing variations of the "RGD" integrin binding sequence known to affect cellular attachment, biologically active ligands, and substances that enhance or exclude particular varieties of cellular or tissue ingrowth such as bone morphogenetic proteins (e.g., BMPs 1-7), growth differentiation factors (e.g., GDF-5, GDF-7, and GDF-8), epidermal growth factor (EGF), fibroblast growth factor (e.g., FGF 1-9), platelet derived growth factor (PDGF), insulin like growth factors (IGF-I and IGF-II), transforming growth factors (e.g., TGF-βI-III), YIGSR peptides, glycosaminoglycans (GAGs), hyaluronic acid (HA), integrins, selectins, cadherins, vascular endothelial growth factor (VEGF); and other naturally derived or genetically engineered proteins, polysaccharides, glycoproteins, or lipoproteins. The agent may also be a combination of any of the above-mentioned agents. See, e.g., PCT/US09/44117. Encapsulating a therapeutic agent or biological material, or the combination of them, is desirous because the encapsulated product can be used for numerous biomedical purposes.

In some embodiments, the active agent may also be an organism such as a fungus, plant, animal, bacterium, or a virus (including bacteriophage). Moreover, the active agent may include neurotransmitters, hormones, intracellular signal transduction agents, pharmaceutically active agents, toxic agents, agricultural chemicals, chemical toxins, biological toxins, microbes, and animal cells such as neurons, liver cells, and immune system cells. The active agents may also include therapeutic compounds, such as pharmacological materials, vitamins, sedatives, hypnotics, prostaglandins and radiopharmaceuticals.

Exemplary cells suitable for use herein may include, but are not limited to, progenitor cells or stem cells, smooth muscle cells, skeletal muscle cells, cardiac muscle cells, epithelial cells, endothelial cells, urothelial cells, fibroblasts, myoblasts, oscular cells, chondrocytes, chondroblasts, osteoblasts, osteoclasts, keratinocytes, kidney tubular cells, kidney basement membrane cells, integumentary cells, bone marrow cells, hepatocytes, bile duct cells, pancreatic islet cells, thyroid, parathyroid, adrenal, hypothalamic, pituitary, ovarian, testicular, salivary gland cells, adipocytes, and precursor cells. The active agents can also be the combinations of any of the cells listed above. See also WO 08/106,485; PCT/US2009/059547; WO 07/103,442.

Exemplary antibodies that may be incorporated in silk fibroin include, but are not limited to, abciximab, adalimumab, alemtuzumab, basiliximab, bevacizumab, cetuximab, certolizumab pegol, daclizumab, eculizumab, efalizumab, gemtuzumab, ibritumomab tiuxetan, infliximab, muromonab-CD3, natalizumab, ofatumumab omalizumab, palivizumab, panitumumab, ranibizumab, rituximab, tositumomab, trastuzumab, altumomab pentetate, arcitumomab, atlizumab, bectumomab, belimumab, besilesomab, biciromab, canakinumab, capromab pendetide, catumaxomab, denosumab, edrecolomab, efungumab, ertumaxomab, etaracizumab, fanolesomab, fontolizumab, gemtuzumab ozogamicin, golimumab, igovomab, imciromab, labetuzumab, mepolizumab, motavizumab, nimotuzumab, nofetumomab merpentan, oregovomab, pemtumomab, pertuzumab, rovelizumab, ruplizumab, sulesomab, tacatuzumab tetraxetan, tefibazumab, tocilizumab, ustekinumab, visilizumab, votumumab, zalutumumab, and zanolimumab. The active agents can also be the combinations of any of the antibodies listed above.

Exemplary antibiotic agents include, but are not limited to, actinomycin; aminoglycosides (e.g., neomycin, gentamicin, tobramycin); β-lactamase inhibitors (e.g., clavulanic acid, sulbactam); glycopeptides (e.g., vancomycin, teicoplanin, polymixin); ansamycins; bacitracin; carbacephem; carbapenems; cephalosporins (e.g., cefazolin, cefaclor, cefditoren, ceftobiprole, cefuroxime, cefotaxime, cefipeme, cefadroxil, cefoxitin, cefprozil, cefdinir); gramicidin; isoniazid; linezolid; macrolides (e.g., erythromycin, clarithromycin, azithromycin); mupirocin; penicillins (e.g., amoxicillin, ampicillin, cloxacillin, dicloxacillin, flucloxacillin, oxacillin, piperacillin); oxolinic acid; polypeptides (e.g., bacitracin, polymyxin B); quinolones (e.g., ciprofloxacin, nalidixic acid, enoxacin, gatifloxacin, levaquin, ofloxacin, etc.); sulfonamides (e.g., sulfasalazine, trimethoprim, trimethoprim-sulfamethoxazole (co-trimoxazole), sulfadiazine); tetracyclines (e.g., doxycyline, minocycline, tetracycline, etc.); monobactams such as aztreonam; chloramphenicol; lincomycin; clindamycin; ethambutol; mupirocin; metronidazole; pefloxacin; pyrazinamide; thiamphenicol; rifampicin; thiamphenicl; dapsone; clofazimine; quinupristin; metronidazole; linezolid; isoniazid; piracil; novobiocin; trimethoprim; fosfomycin; fusidic acid; or other topical antibiotics. Optionally, the antibiotic agents may also be antimicrobial peptides such as defensins, magainin and nisin; or lytic bacteriophage. The antibiotic agents can also be the combinations of any of the agents listed above. See also PCT/US2010/026190.

Exemplary enzymes suitable for use herein include, but are not limited to, peroxidase, lipase, amylose, organophosphate dehydrogenase, ligases, restriction endonucleases, ribonucleases, DNA polymerases, glucose oxidase, laccase, and the like. Interactions between components may also be used to functionalize silk fibroin through, for example, specific interaction between avidin and biotin. The active agents can also be the combinations of any of the enzymes listed above. See U.S. patent application Ser. No. 61/226,801.

When introducing therapeutic agents or biological material into the silk fibroin, other materials known in the art may also be added with the agent. For instance, it may be desirable to add materials to promote the growth of the agent (for biological materials), promote the functionality of the agent after it is released from the silk mats, or increase the agent's ability to survive or retain its efficacy during the period it is embedded in the silk. Materials known to promote cell growth include cell growth media, such as Dulbecco's Modified Eagle Medium (DMEM), fetal bovine serum (FBS), non-essential amino acids and antibiotics, and growth and morphogenic factors such as fibroblast growth factor (FGF), transforming growth factors (TGFs), vascular endothelial growth factor (VEGF), epidermal growth factor (EGF), insulin-like growth factor (IGF-I), bone morphogenetic growth factors (BMPs), nerve growth factors, and related proteins may be used. Growth factors are known in the art, see, e.g., Rosen & Thies, CELLULAR & MOLECULAR BASIS BONE FORMATION & REPAIR (R.G. Landes Co., Austin, Tex., 1995). Additional options for delivery via the silk mats include DNA, siRNA, antisense, plasmids, liposomes and related systems for delivery of genetic materials; peptides and proteins to activate cellular signaling cascades; peptides and proteins to promote mineralization or related events from cells; adhesion peptides and proteins to improve silk mats-tissue interfaces; antimicrobial peptides; and proteins and related compound.

Additional biocompatible material may also be combined with the functionalized silk fibroin materials, such as polyethylene glycol (see PCT/US09/64673), collagen, fibronectin, keratin, polyaspartic acid, polylysine, alginate, chitosan, chitin, hyaluronic acid, pectin, polycaprolactone, polylactic acid, polyglycolic acid, polyhydroxyalkanoates, dextrans, polyanhydrides, glycerol (see PCT/US2009/060135), and other biocompatible polymers, see WO 04/0000915. Alternatively, the silk may be mixed with hydroxyapatite particles, see PCT/US08/82487. As noted herein, the silk fibroin can be of recombinant origin, which provides for further modification of the silk such as the inclusion of a fusion polypeptide comprising a fibrous protein domain and a mineralization domain, that are used to form an organic-inorganic composite. These organic-inorganic composites can be constructed from the nano- to the macro-scale depending on the size of the fibrous protein fusion domain used, see WO 06/076711. See also U.S. patent application Ser. No. 12/192,588.

The silk-fibroin embedded active agents or biological materials may be suitable for long term storage and stabilization of the cells and/or active agents. Cells and/or active agents, when incorporated in the silk mats, can be stable (i.e., maintaining at least 50% of residual activity) for at least 30 days at room temperature (i.e., 22° C. to 25° C.) and body temperature (37° C.). Hence, temperature-sensitive active agents, such as some antibiotics, can be stored in silk mats without refrigeration. Importantly, temperature-sensitive bioactive agents can be delivered (e.g., through injection) into the body in silk mats and maintain activity for a longer period of time than previously imagined. See, e.g., PCT/US2010/026190.

The silk-fibroin embedded active agents (e.g., therapeutic agents) or biological materials are suitable for a biodelivery device. Techniques for using silk fibroin as a biodelivery device may be found, for example, in U.S. patent application Ser. Nos. 10/541,182; 11/628,930; 11/664,234; 11/407,373; PCT/US07/020,789; PCT/US08/55072; PCT/US09/44117. Some embodiments of the present invention relate to the utility of silk-fibroin embedded therapeutic agents or biological materials as drug delivery systems for potential utility in medical implants, tissue repairs and for medical device coating. See PCT/US10/041,953.

The functionalized silk structures described herein enable a biodelivery vehicle to have a controlled release. Controlled release permits dosages to be administered over time, with controlled release kinetics. In some instances, delivery of the therapeutic agent or biological material is continuous to the site where treatment is needed, for example, over several weeks. Controlled release over time, for example, over several days or weeks, or longer, permits continuous delivery of the therapeutic agent or biological material to obtain preferred treatments. The controlled delivery vehicle is advantageous because it protects the therapeutic agent or biological material from degradation in vivo in body fluids and tissue, for example, by proteases. See, e.g., PCT/US09/44117.

Controlled release of the active agent from the functionalized silk may be designed to occur over time, for example, for greater than about 12 hours or 24 hours, inclusive; greater than 1 month, or 2 months, or 5 months, inclusive. The time of release may be selected, for example, to occur over a time period of about 12 hours to 24 hours, or about 12 hours to 1 week, inclusive. In another embodiment, release may occur for example on the order of about 1 month to 2 months, inclusive. The controlled release time may be selected based on the condition treated. For example, a particular release profile may be more effective where consistent release and high local dosage are desired.

Additionally, a therapeutic active agent can be combined with functionalized silk material and a pharmaceutically acceptable carrier. Any pharmaceutical carrier can be used that does not dissolve the silk matrix in an undesired fashion. The active agents may be present as a liquid, a finely divided solid, or any other appropriate physical form. Optionally, the matrix can include one or more additives, such as diluents, carriers, excipients, stabilizers or the like.

The amount of active agent will depend on the particular drug being employed and medical condition being treated. For example, the amount of drug may represent about 0.001% to about 70%, or about 0.001% to about 50%, or about 0.001% to about 20% by weight of the material. Upon contact with body fluids the drug can be released.

The present invention may be as defined in any one of the following numbered paragraphs:

1. A method of functionalizing a silk fibroin in an aqueous solution with a bioactive agent, comprising: reacting a silk fibroin molecule with an avidin in an aqueous solution to form a silk fibroin-avidin conjugate, wherein avidin is linked to the silk fibroin protein through a covalent bond; providing a biotinylated active agent; and contacting the silk fibroin-avidin conjugate with the biotinylated active agent in an aqueous solution to form a silk fibroin-avidin-biotin-bioactive agent conjugate, wherein the biotinylated bioactive agent is linked to the silk fibroin protein-avidin conjugate through avidin-biotin interaction.
2. A method of functionalizing a silk fibroin protein in an aqueous solution with at least one active agent, comprising: reacting a silk fibroin molecule with biotin in an aqueous solution to form a silk fibroin-biotin conjugate, wherein biotin is linked to the silk fibroin protein through a covalent bond; providing a biotinylated avidin-linked active agent formed by linking avidin to a biotinylated active agent; and contacting the silk fibroin protein-biotin conjugate with the avidin-linked biotinylated active agent in an aqueous solution to form a silk fibroin-biotin-avidin-biotin-active agent conjugate, wherein the avidin-biotinylated active agent is linked to the silk fibroin-biotin conjugate through avidin-biotin interactions.
3. The method of paragraph 1 or 2, further comprising the step of forming the aqueous silk fibroin-biotin-avidin-biotin-active agent conjugate into a film, porous matrix, nanoparticle, microparticle, sponge, or gel.
4. The method of paragraphs 1 to 3, wherein the active agent is selected from the group consisting of cell binding domains, cell signaling factors, proteins, antibodies or portions or fragments thereof, peptides, nucleic acids, PNA, aptamers, hormones, growth factors, cytokines, enzymes, antibiotics, antivirals, small molecules, and combinations thereof.
5. The method of paragraph 4, wherein the active agent is a growth factor or an antibody.
6. A silk fibroin protein functionalized with a active agent, prepared by the method according to paragraphs 1 to 3.
7. An active agent-functionalized silk material comprising silk fibroin functionalized with an active agent, wherein the silk material is prepared from silk fibroin solution comprising silk fibroin linked to at least one active agent through avidin-biotin linkage.
8. The active agent-functionalized silk material of paragraph 7, wherein the functionalized silk fibroin is a silk fibroin-avidin-biotin-active agent conjugate prepared via an avidin-biotin interaction between a silk fibroin-avidin conjugate and a biotinylated active agent in an aqueous solution.
9. The active agent-functionalized silk material of paragraph 7, wherein the functionalized silk fibroin is a silk fibroin-biotin-avidin-biotin-active agent conjugate prepared via an avidin-biotin interaction between a silk fibroin-biotin conjugate and an avidin-biotinylated active agent in an aqueous solution.
10. The silk material of paragraphs 7 to 9, wherein the silk material is a gel, film, porous scaffold, sponge, nanoparticle, or microparticle.
11. A method of functionalizing the surface of a silk particle with a bioactive agent, comprising: providing a silk particle; providing a biotinylated bioactive agent; reacting the silk particle with avidin in an aqueous solution to form a silk particle-avidin conjugate, wherein avidin is linked to the surface of silk particle through a covalent bond; and contacting the silk particle-avidin conjugate with the biotinylated bioactive agent to form a silk particle-avidin-biotin-bioactive agent conjugate, wherein the biotinylated bioactive agent is linked to the silk particle-avidin conjugate through avidin-biotin interaction.
12. The method of paragraph 11, wherein the silk particle is silk microsphere or nano sphere.
13. The method of paragraph 11, wherein the silk particle is silk film or diazo-silk film.
14. The method of paragraph 11, wherein the silk particle is treated with BSA before the step of linking the silk particle to avidin.
15. The method of paragraph 11, wherein the silk particle is treated with detergent after the step of linking the silk particle to avidin.
16. The method of paragraph 1, 2, 3 or 11, wherein avidin or biotin is linked to the silk fibroin protein molecule or the silk particle via a carbodiimide coupling reaction using 1-Ethyl-3-(3-dimethylaminopropyl)-carbodiimide (EDC).
17. The method of paragraphs 1, 2, 3 or 11, wherein the avidin is avidin, NeutrAvidin or Streptavidin.

18. The method of paragraphs 1, 2, 3 or 11, further comprising the step of contacting said functionalized silk with a cell.
19. The method of paragraphs 11, further comprising the step of adding said functionalized silk particle to a silk fibroin solution.
20. The method of paragraphs 11 or 19 further comprising contacting said silk fibroin solution with a cell.
21. The method of paragraphs 19 or 20 further comprising initiating gelation of said silk fibroin solution.

EXAMPLES

Example 1

Silk Fibroin (SF) Purification

Cocoons of *B. mori* silkworm silk were supplied by Tajima Shoji Co. (Yokohama, Japan). 1,2-Dioleoyl-sn-glycero-3-phosphocholine (DOPC) was purchased from Avanti Polar Lipids (Alabaster, Ala.). TMB (3,3'5,5' Tetramethylbenzidine) solution was purchased from BioFX laboratories (Owing Mills, Md.). NeutrAvidin, FITC-NeutrAvidin, horseradish peroxidase (HRP), biotin-HRP, 1-ethyl-3-[3-dimethylaminopropyl]carbodiimide hydrochloride (EDC), N-hydroxysuccinimide (NHS), and hydroxylamine hydrochloride were purchased from Pierce Biotechnology (Rockford, Ill.). Atto 610-Biotin, bovine serum albumin (BSA), and other chemicals were purchased from Sigma Aldrich (St. Louis, Mo.). T-lymphocytic cell line Jurkat was obtained from ATTC (Manassas, Va.). All cell culture medium components were purchased from Invitrogen (Carlsbad, Calif.).

Silk fibroin aqueous stock solutions were prepared as described previously. See Sofia et al., 54 J. Biomed. Mater. Res. A 139-48 (2001). Briefly, cocoons of *B. mori* were boiled for 20 min in an aqueous solution of 0.02 M $NaCO_3$, and then rinsed thoroughly with purified $H_2O$. After drying, the extracted silk fibroin was dissolved in a 9.3 M LiBr solution at 60° C. for 4 hr, yielding a 20% (w/v) solution. The resulting solution was dialyzed against distilled water using Slide-a-Lyzer dialysis cassettes (MWCO 3,500, Pierce) for 3 days to remove the residual salt. The solution was optically clear after dialysis and was centrifuged to remove the small amounts of silk aggregates that formed during the process. The final concentration of silk fibroin aqueous solution was approximately 8% (w/v). This concentration was determined by drying the solution of a known volume and weighing the residual solid.

Example 2

Coupling of NeutrAvidin to Silk Fibroin Protein in Solution

EDC coupling reaction: Silk fibroin solution was diluted to 2% (w/v) with water, and 3 ml of the diluted solution was injected into a 0.5-3 ml Slide-A-Lyzer (3.5K MWCO) dialysis cassette (Pierce Chemicals, Ill.) and dialyzed against 1 L of 0.1 M 2-(morpholino) ethanesulfonic acid (MES) solution (pH 5.6) (Pierce Chemicals) overnight. Two (2) ml of the dialyzed solution was transferred to a glass beaker, followed by adding 16 mg EDC and 44 mg NHS into the solution. The reaction lasted for 15 min, with slow stirring in order to convert the free carboxyl groups on silk fibroin proteins to amine-reactive NHS esters. After the reaction, 3 µl of β-mercaptoethanol was added to quench the unreacted EDC. The solution was then mixed with 20 mg of NeutrAvidin (molar ratio between NeutrAvidin:silk fibroin about 3:1) and allowed to react for 30 min under slow stirring at room temperature, before adding 1 mg hydroxylamine hydrochloride to quench the reaction. The resulting solution was injected into a 0.5-3 ml Slide-A-Lyzer dialysis cassette (3.5K MWCO) and dialyzed against 1 L of water for 5 hr, replenishing water every hr. The final concentration of NeutrAvidin-coupled silk fibroin was ~2% (w/v) determined by the same method described above.

Gelation of NeutrAvidin-silk solution: NeutrAvidin-coupled silk fibroin solution was gelled using sonication as described previously. Wang, 2008. Briefly, 0.5 mL of NeutrAvidin-coupled silk solution (about 2% w/v) in a 1.5 mL Eppendorf tube was sonicated with a Branson 450 Sonifier (Branson Ultrasonics Co., Danbury, Conn.), using a 1/8" (3.175 mm) diameter Tapered Microtip (Part #101-148-062). The sonication was performed at 15% amplitude with the sonication time varying from 15-60 sec. The solutions after sonication were incubated at 37° C. and the sol-gel transition was monitored visually by turning over the tube and checking the opacity change of the solution, as discussed in Wang et al., 2008.

Quantification of bound NeutrAvidin using Atto 610-Biotin: Atto 610-Biotin (ATTO-TEC GmbH, Siegen, Germany), a fluorescently labeled biotin, has an excitation maximum at 610 nm and maintains high binding affinity to NeutrAvidin. 1 mg of Atto 610-Biotin was dissolved in 100 µl dimethylformamide to prepare the stock solution then stored at 4° C. The stock solution was diluted 100-fold with Dulbecco's phosphate buffer, pH 7.2 (Invitrogen, Carlsbad, Calif.). Aliquots of silk-NeutrAvidin gel prepared as described above (0, 10, 20, 30, 50, 100 µl of gel containing 0, 0.5, 1, 1.5, 2.5, 5 nmol of silk fibroin, respectively, assuming that silk molecules have an average molecular weight of 350 KDa), was pipetted into an Eppendorf tube, followed by adding 1 ml of Atto 610-Biotin solution (containing 12.5 nmol of biotin). Alternatively, aliquots of 30 µl sonicated gel were placed in Eppendorf tubes, followed by adding 1 ml of Atto 610-Biotin with concentrations ranging from 15 µM to 250 µM. The tubes were incubated for 30 min at room temperature on a shaker, and then centrifuged at 12,000 rpm for 10 min (Eppendorf microcentrifuge Model 5417R). The supernatant was transferred to an empty tube and subjected to UV absorbance measurement. The precipitant (pellet) was washed several times with 1 ml of PBS buffer solution until UV absorbance of the supernatant was about equal to the background signal. The amount of Atto 610-Biotin in all supernatants was calculated using a standard curve of Atto 610-Biotin with known concentrations. The amount of Atto 610-Biotin bound to NeutrAvidin-silk gel was obtained by subtracting the amount in the supernatants from the total amount used originally. Silk hydrogel (2% w/v) without NeutrAvidin coupling was subjected to the same analysis, and the result subtracted to obtain absolute amount of bound Atto 610-biotin-NeutrAvidin-silk gel.

Binding of biotin-HRP and HRP to NeutrAvidin-silk: Five (5) mg of biotin-HRP or HRP was added to 0.5 ml of 2% NeutrAvidin-silk solution obtained as described above. The molar ratio between HRP and silk was approximately 4:1. The mixture was subjected to sonication to induce silk gelation. Subsequently, aliquots of silk gel (100 µl) were transferred to empty tubes supplemented with 1 ml of PBS buffer, pH 7.0. After vortexing for 1 min, the tubes were centrifuged at 12,000 rpm for 10 min (Eppendorf 5417R). The supernatant was then transferred to empty tubes, and the precipitant was washed twice more using the same centrifugation conditions, and all the supernatants were collected.

The same procedure was repeated for binding biotin-HRP or HRP to silk fibroin in solution with no NeutrAvidin conjugated to silk protein. The resulting supernatants were collected and used as controls.

All the supernatants from above procedures were assayed for HRP. For each assay, 5 µl of supernatant was mixed with 100 µl of TMB (HRP substrate) in 96-well standard microplate wells for 1 min at room temperature. The reaction was stopped by the addition of 100 µl 0.1 M sulfuric acid. TMB was oxidized during the enzymatic degradation of $H_2O_2$ by HRP. The oxidized product of TMB has a deep blue color and turns to yellow after addition of the acidic stop solution. Absorbance was detected at 450 nm using a VERSAMAX™ microplate reader (Molecular Devices, Sunnyvale, Calif.), and the HRP activity was calculated based on a standard plot of HRP with known concentrations.

Secondary structure characterization: Fourier transform infrared (FTIR) spectroscopy was used to determine the secondary structural changes of NeutrAvidin-silk before and after gelation, using unmodified silk as a control. For this, 2% (w/v) silk and NeutrAvidin-silk solution was induced to form a gel as described above. The gels as well as the original solutions were lyophilized and then subjected to FTIR analysis using a JASCO FTIR 6200 Spectrometer (JASCO, Tokyo, Japan). After determining and subtracting background signals the samples were scanned 64 times from 400 $cm^{-1}$ to 4000 $cm^{-1}$ with a resolution of 4 $cm^{-1}$. The data obtained were analyzed using the software provided by the manufacturer. The spectra of interest were compared for absorption bands of random coil (1638 $cm^{-1}$ to 1655 $cm^{-1}$) and β-sheet (1616 $cm^{-1}$ to 1637 $cm^{-1}$) structure. Wang et al. 2008.

Chemical stability: Silk and NeutrAvidin-silk solution with a concentration of 2% (w/v) and volume of 0.5 ml were sonicated with 15% amplitude for 30 seconds. After lyophilization, an aliquot of the dried gel of about 5 mg was weighed and immersed in 1 ml of the following solutions in a 1.5-ml Eppendorf tube: 6 M, 4M, 2 M guanidinium hydrochloride (GdmCl), 8 M, 4 M urea, 1% Triton X-100. Samples were prepared in triplicates. After incubation at room temperature for 3 days, the samples were centrifuged at 12,000 rpm for 10 min (Eppendorf 5417R centrifuge) and the supernatant solution was removed. The pellets were suspended in 1 ml water and washed for 2 hr by shaking at room temperature. After washing three times, the pellets were dried at 60° C. and weighed. The mass of the remaining gel was then compared with its original mass to estimate chemical stability.

Example 3

Coupling of NeutrAvidin to Silk Microspheres

Preparation of silk microspheres: silk microspheres were prepared using liposomes as templates. Wang et al., 2007. Briefly, 200 mg of DOPC was dissolved in 1 ml chloroform in a glass tube and dried into a film under a flow of nitrogen gas. One (1) ml of 8% (w/v) silk fibroin solution was added to hydrate the lipid film, and the mixture was diluted to 4 ml with water and transferred to a plastic tube. The sample was frozen in liquid nitrogen for 15 min and then thawed at 37° C. for 15 min. This freeze-thaw cycle was repeated three times, yielding smaller vesicles with a more homogeneous size distribution. Wang et al., 2007. With rapid stirring, the thawed solution was slowly pipetted into a glass beaker containing 50 ml $H_2O$. The resulting solution was transferred to a plastic tube and lyophilized for 3 days. The lyophilized material was then treated with 30 ml MeOH for 15 min with gentle shaking at room temperature, followed by centrifugation at 10,000 rpm for 5 min at 4° C. The pellet obtained was dried in air and stored at room temperature. Generally, the dried pellet was suspended in MES buffer, before the coupling reaction. The clustered microspheres were dispersed by ultrasonication for 10 sec at 30% amplitude (approximately 20 W) using a Branson 450 ultrasonicator (Branson Ultrasonics Co., Danbury, Conn.).

EDC coupling reaction: The EDC coupling reaction of NeutrAvidin to silk microspheres was similar to that described above for coupling reaction of silk fibroin protein in solution. Briefly, silk microspheres were prepared and suspended in MES buffer to reach a final concentration of 2% (w/v). Eight (8) mg of EDC and 22 mg of NHS were then added to 1 ml of the microsphere suspension and the mixture incubated for 15 min. Ten (10) mg of NeutrAvidin was then added to 1 ml of 2% (w/v) silk microsphere suspension. The molar ratio between the NeutrAvidin and silk was about 3:1. After 5 hr incubation, the reaction was stopped by adding 1 mg hydroxylamine HCl to the solution. The solution was then centrifuged at 10,000 rpm for 5 min (Eppendorf 5417R centrifuge), and the pelleted microspheres were washed three times by centrifugation in ultra pure water to remove all unbound biotin. The resulting microspheres were suspended in PBS buffer (pH 7.2).

Reducing non-specific binding of NeutrAvidin: Different techniques can be used in modulating (e.g., reducing) the non-specific binding of avidin to silk microspheres, including a pretreatment BSA blocking method and a post-treatment detergent washing method.

For the BSA blocking method, after washing the silk microspheres by centrifugation and before the coupling reaction, samples were re-suspended in 10 mg/ml BSA and incubated at room temperature overnight. The microspheres were then centrifuged, and re-suspended in PBS to a final concentration of 10 mg/ml, and were then used for EDC coupling reaction with NeutrAvidin as described herein.

For the detergent washing method, the same EDC coupling procedure was performed as described herein, then after coupling with NeutrAvidin, samples were washed thrice with 1% (v/v) Triton X-100 by centrifugation at 10,000 rpm for 5 min (Eppendorf 5417R centrifuge). The resulting samples are washed twice with ultra-pure water before finally being re-suspended in PBS buffer.

To investigate further the effect of non-specific binding of BSA to silk microspheres, fluorescent tetramethylrhodamine conjugated BSA (TMR-BSA) was used, and binding was determined both visually and quantitatively. Five (5) mg of lyophilized silk microspheres were immersed in 0.1 ml, 10 mg/ml TMR-BSA solution. After incubating for 2 hr at room temperature, the microspheres were centrifuged at 10,000 rpm for 5 min. The pellet was suspended in 100 µl water. An aliquot of the suspension (50 µl) was centrifuged again, and the pellet washed twice with 1 ml water using the same centrifugation conditions. The washed microspheres were suspended in 50 µl water. Both washed and non-washed samples were then visualized using a confocal laser scanning microscope (TCS Leica SP2, Welzlar, Germany) with Leica Confocal Software, version 2.5 (Leica Microsystems, Heidelberg, Germany). To quantitatively determine the binding, low concentrations of TMR-BSA were used. Ten (10) mg of lyophilized silk microspheres were suspended in 0.5 ml TMR-BSA solution with concentrations of 16, 80 and 400 µg/ml. The samples were shaken for 2 hr at room temperature and then centrifuged at 10,000 rpm for 5 min. The supernatants were moved to a black 96-well plate (CORNING®COSTAR® flat bottom plate) for fluorescence measurement with excitation and emission wavelengths of 555 nm and 580 nm, respectively. The same amount of original TMR-BSA solution was also added to empty wells to serve as standards. The amount of bound TMR-BSA was calculated by subtracting the amount in the supernatants from the original.

Coupling of anti-CD3 antibody on silk microspheres via NeutrAvidin/biotin reaction: Biotinylated anti-CD3 antibody was dissolved in PBS buffer, pH 7.2, to make a 0.5 mg/ml stock solution. The solution was aliquot and stored at −20° C. 200 µl of the biotinylated anti-CD3 antibody stock solution was mixed with 250 µl of NeutrAvidin-coupled silk microsphere suspension. The mixture was incubated for 20 min at room temperature and then centrifuged at 10,000 rpm for 5 min (Eppendorf 5417R centrifuge). The microspheres were washed two more times with 1 ml PBS buffer each time, and the final suspension was stored at 4° C.

Targeting of anti-CD3 antibody-coupled silk microspheres to lymphocytes: Coupling reactions were performed as described above, except that the FITC conjugated NeutrAvidin (Pierce, Rockford, Ill.) was used instead of NeutrAvidin. The T-lymphocytic cell line Jurkat (ATCC, TIB-152) was cultivated in RPMI 1640 supplemented with antibiotics (100 U/mL penicillin and 100 mg/mL streptomycin), L-glutamine (2 mM) and 10% heat-inactivated fetal calf serum (FCS). A cell suspension was prepared at the concentration of $2 \times 10^5$ cells/ml. Two (2) ml of the cell suspension was added to each well of a 12-well plate and incubated with 200 µg of anti-CD3 antibody conjugated silk microspheres which were prepared by binding FITC-NeutrAvidin-coupled silk microspheres with biotinylated anti-CD3 antibody. The plate was incubated at 37° C. for 2 hr, and then the cells were centrifuged at 1,000 rpm for 10 min (Eppendorf 5417R centrifuge) and re-suspended in PBS buffer (pH 7.2). Cells were imaged using a confocal laser scanning microscope (TCS Leica SP2, Welzlar, Germany) with Leica Confocal Software, version 2.5 (Leica Microsystems, Heidelberg, Germany). To estimate the cell viability before and after adding microspheres, 0.5 ml of above cell suspension ($2 \times 10^5$ cells/ml) was mixed with 0.1 ml of 0.4% Trypan Blue Stain (Sigma-Aldrich), and the mixture was added to fill a hemocytometer for cell counting. Non-viable cells were stained blue and the viable cells excluded the stain.

Statistics: Statistical analysis was performed by one-way analysis of variance (ANOVA) and Student-New-man-Keuls Multiple Comparisons Test. Differences were considered significant when $p \leq 0.05$ and very significant when $p \leq 0.01$.

Example 4

Conjugation of Antibodies to Silk or Diazo-Silk Films Via Avidin-Biotin

Lyophilysed silk fibroin was dissolved to a final concentration of 5% w/v in HFIP (1,1,1,3,3,3-Hexafluoroisopropanol) and cast as thin films (30 µl/well in 96-well plates). Plates were kept in an air hood overnight to allow solvent evaporation. The next day, films were treated with 90% v/v methanol solution in water for 10 min. Subsequently, films were washed three times with water (200 µl/well). Films were then dried overnight in the hood.

Figure 8:
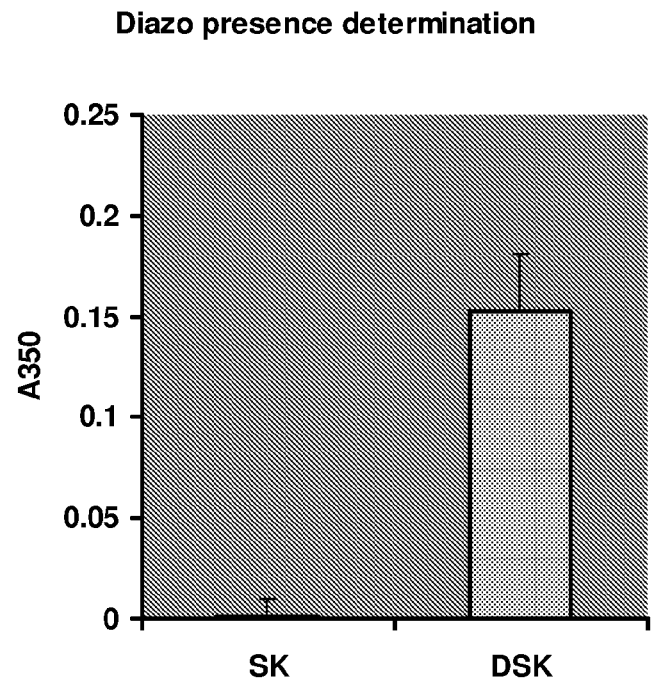
FIG. 8 shows the results of spectrophotometric evaluation of successful diazonium coupling (SK=silk fibroin films; DSK=diazonium coupled silk fibroin films).

Diazonium salt coupling: The diazonium salt was prepared from solutions (a) and (b) as follows: (a) 4-amino benzoic acid (130 mg) was dissolved in 5 ml acetonitrile then mixed with p-toluene sulfonic acid (760 mg) dissolved in 2.5 ml water and kept on ice. Separately, (b) sodium nitrite (170 µl) was added to 2.37 ml water and kept on ice for ten minutes. Subsequently, the (a) and (b) solutions were mixed and kept on ice for 30 min. The diazonium salt solution was then decanted into a trough and a multichannel pipetter was used to add 100 µl salt solution to each silk film-containing well. For coupling, the 96-well plates were incubated for 30 min at 4° C., then washed with water (200 µl/well) three times. Successful diazonium coupling could be visually (appearance of orange color) and spectrophotometrically evaluated (A 350 nm) (FIG. 8).

Figure 9:
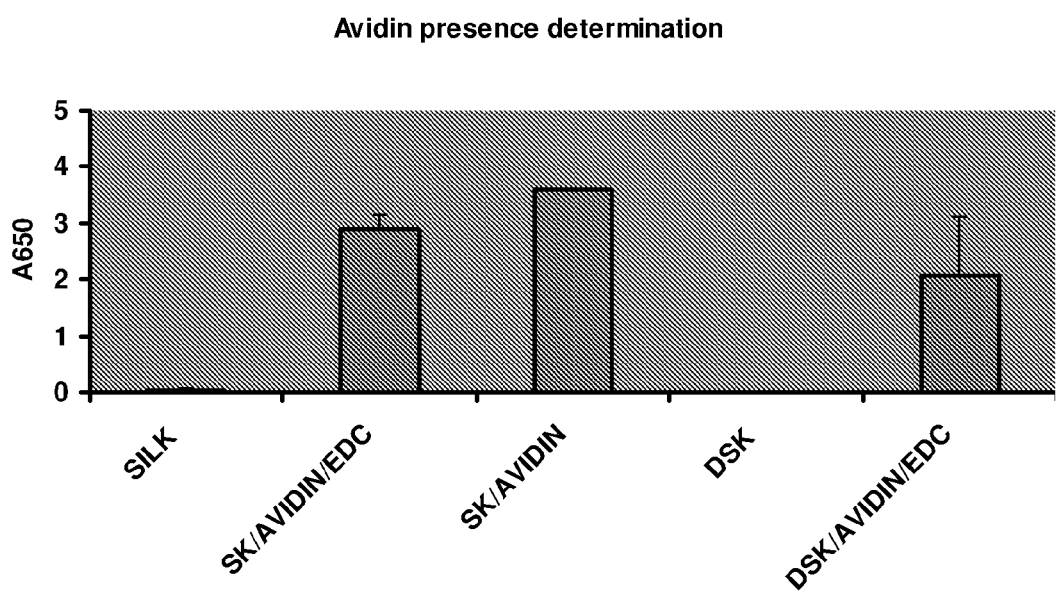
FIG. 9 presents the detection of avidin, through a biotin-HRP/TMB system, indicating that avidin can be both specifically and non-specifically coupled to silk (SILK: untreated control films; SK/AVIDIN/EDC: silk films coupled with avidin via EDC; SK/AVIDIN: silk films treated with avidin in the absence of EDC; DSK: untreated control diazo-silk films; DSK/AVIDIN/EDC: diazo-silk films coupled with avidin via EDC).

Silk-avidin coupling: An EDC (1-Ethyl-3-[3-dimethylaminopropyl]carbodiimide hydrochloride) solution in 1×MES buffer, pH 6 at a final concentration of 0.5 M was prepared and added to several silk film-coated wells. The 96-well plate was then incubated for 30 min at room temperature. NeutrAvidin (10 mg) was reconstituted with 3.5 ml water. After complete dissolution, the NeutrAvidin solution was mixed with 10×PBS, to reach a final concentration of 42 µM NeutrAvidin in 1×PBS, pH 7.4. The plate was then blotted and neutravidin (42 µM solution, 100 µl/well) was added to wells coated with silk fibroin or diazo-silk fibroin±EDC. After 2 hr incubation, the wells were washed three times with water (200 µl/well). The efficiency of neutravidin attachment to silk or diazosilk (±EDC) was tested by using a biotin-horseradish peroxidase (biotin-HRP)/TMB system. Briefly, 50 µl of biotin-HRP (VECTASTAIN® detection kit, Vector Labs., Burlingame, Calif.) was added to 10 ml of 1×PBS, pH 7.4. Next, 100 µl of the biotin-HRP solution was added to wells and incubated for 30 min at room temperature. After incubation, wells were washed three times with 1×PBS, pH 7.4. To each well, 100 µl of TMB (3,3',5,5' tetramethyl benzidine) was added and the plate was incubated for 10 min at room temperature. Successful avidin attachment to films was indicated by the development a blue color, detectable at A 650 (FIG. 9).

Antibody-biotin counjugation: Sulfo-LC-NHS biotin was dissolved in water to a final concentration of 1 mM. To 100 µl ALEXA FLUOR®-conjugated anti-GFP antibody (2 mg/ml) was added 27 µl of biotin solution. This solution was incubated at room temperature for 2 hr. Subsequently, water was added to a final volume of 250 µl and purified using NAP-5 column purification to remove any unreacted biotin. $^1$H-NMR detection of the antibody-biotin was not possible because of the low sample concentration (typically 10 mg/ml sample is needed for successful NMR detection).

Figure 10:
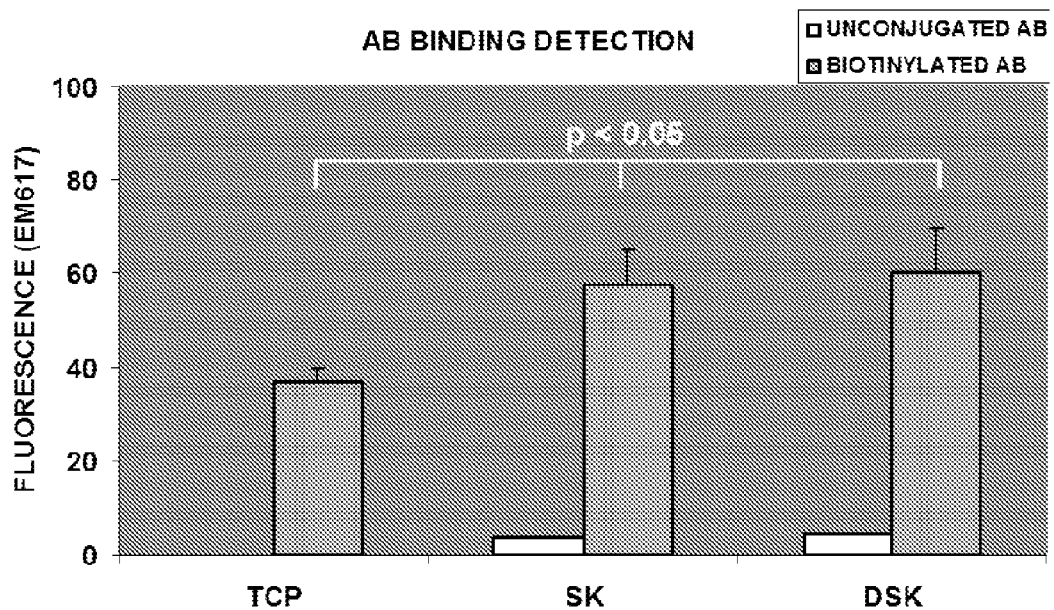
FIG. 10 shows the detection of surface bound antibodies (Alexa-tagged anti-GFP) indicating that biotinylation of the antibody is needed for surface attachment to the avidin coated substrates. Surface antibody binding was significantly enhanced (~50%) on silk/avidin or diazo-silk/avidin films compared to tissue culture plate/avidin ($p < 0.05$).

Silk-antibody coupling: In preparation for antibody coupling, silk or diazo-silk films treated with avidin as described herein, without EDC, were washed three times with Pierce SuperBlock blocking buffer (Thermo Scientific, Rockford, Ill.). Subsequently, 100 µl of antibody-biotin was added to each well and the plate was incubated for 2 hr at room temperature. Successful coupling of antibody was detected by monitoring for Alexa emission (Ex/em 590/617) (FIG. 10). Although avidin binds nonspecifically to the IMMULON® multi-well plate (uncoated), the results indicate that coating of the wells with silk fibroin or diazo-silk fibroin films, increases the coupling efficiency by 1.5-fold. This finding underlines the potential of silk to enhance antibody conjugation via the avidin-biotin system.

Figure 11:
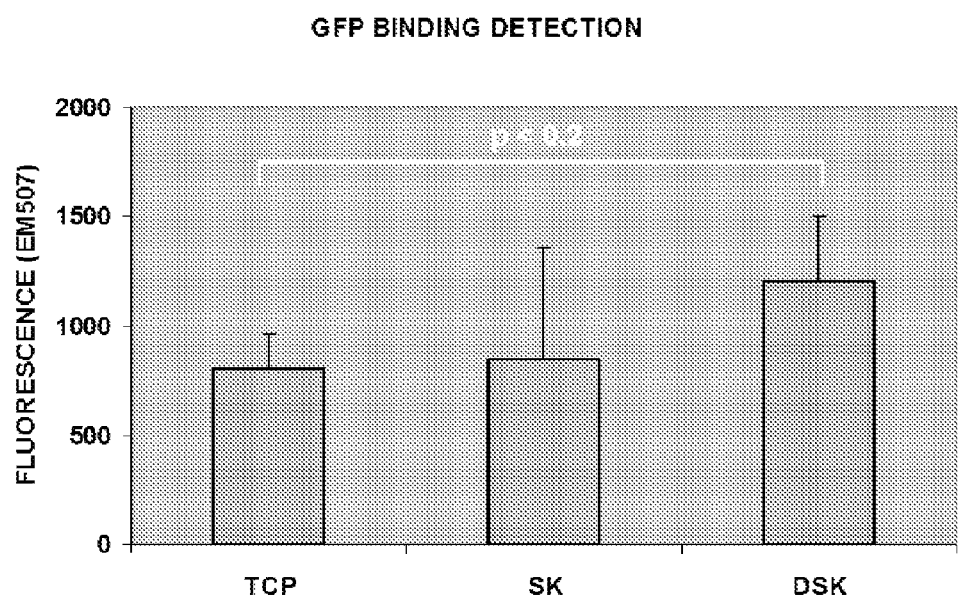
FIG. 11 is a proof of concept assay showing that surface bound antibodies are capable of efficienty trapping their specific antigen (GFP). The extent of antigen recognition appeared similar on tissue culture plate/avidin and silk/avidin surfaces, and slightly increased on diazo-silk/avidin surfaces ($p < 0.2$).

To test the efficacy of the antibody-conjugation system, green fluorescent protein (GFP) solution (100 µl of 1 mg/ml stock solution dissolved in 1.2 ml 1×PBS, pH 7.4) was added to antibody conjugated wells. After 30 min incubation, plates were washed three times with 1×PBS, pH 7.4, and the antigen capturing efficiency was monitored spectrophoto-metrically (ex/em 488/507) (FIG. 11). The results indicated that all antibody containing systems were able to efficiently capture the GFP antigen. The extent of antigen recognition was slightly increased on the diazo-silk coated wells and comparable between the uncoated, avidin-biotin-antibody containing wells and the silk film-avidin-biotin-antibody coated wells.

The results presented herein exemplify the successful conjugation antibodies to silk and diazo-silk films through an avidin-biotin mediated approach. Avidin was bound nonspecifically to silk or diazo-silk. Specific, EDC-mediated avidin attachment can also be achieved. For the purpose of this example, the non-specific avidin binding was found suitable. Silk and diazo-silk film casting enhanced the amount of biotin nonspecifically bound to the surface, thus conferring an increased background for biotin interaction. In order to maintain the availability of the antibody recognition sites upon biotin conjugation, a modified biotin analog was selected, that presented amine reactive functionalities needed for chemical conjugation with the antibody, while also presenting a 22.4 Å spacer arm that, upon antibody-biotin binding to the well surface, allowed the antibody to orient properly for antigen capture. The efficient coupling of antibodies to modified or unmodified silk films was proved by successful detection of antigen (GFP) capture by the system.

We claim:

1. A method of functionalizing a silk fibroin in an aqueous solution with a bioactive agent, comprising:
   reacting a silk fibroin molecule with an avidin in an aqueous solution to form a silk fibroin-avidin conjugate, wherein avidin is linked to the silk fibroin protein through a covalent bond;
   providing a biotinylated active agent; and
   contacting the silk fibroin-avidin conjugate with the biotinylated active agent in an aqueous solution to form a silk fibroin-avidin-biotin-bioactive agent conjugate, wherein the biotinylated bioactive agent is linked to the silk fibroin protein-avidin conjugate through avidin-biotin interactions.

2. A method of functionalizing a silk fibroin protein in an aqueous solution with at least one active agent, comprising:
   reacting a silk fibroin molecule with biotin in an aqueous solution to form a silk fibroin-biotin conjugate, wherein biotin is linked to the silk fibroin protein through a covalent bond;
   providing a biotinylated avidin-linked active agent formed by linking avidin to a biotinylated active agent; and
   contacting the silk fibroin protein-biotin conjugate with the avidin-linked biotinylated active agent in an aqueous solution to form a silk fibroin-biotin-avidin-biotin-active agent conjugate, wherein the avidin-biotinylated active agent is linked to the silk fibroin-biotin conjugate through avidin-biotin interactions.

3. The method of claim 1 or 2, further comprising the step of forming the aqueous silk fibroin-biotin-avidin-biotin-active agent conjugate into a film, porous matrix, nanoparticle, microparticle, sponge, or gel.

4. The method of claim 1 or 2, wherein the active agent is selected from the group consisting of cell binding domains, cell signaling factors, proteins, antibodies or portions or fragments thereof, peptides, nucleic acids, peptid nucleic acid, aptamers, hormones, growth factors, cytokines, enzymes, antibiotics, antivirals, small molecules, and combinations thereof.

5. The method of claim 4, wherein the active agent is a growth factor or an antibody.

6. A silk fibroin protein functionalized with a active agent, prepared by the method according to claim 1 or 2.

7. An active agent-functionalized silk material comprising silk fibroin functionalized with an active agent, wherein the silk material is prepared from silk fibroin solution comprising silk fibroin linked to at least one active agent through avidin-biotin linkage.

8. The active agent-functionalized silk material of claim 7, wherein the functionalized silk fibroin is a silk fibroin-avidin-biotin-active agent conjugate prepared via an avidin-biotin interaction between a silk fibroin-avidin conjugate and a biotinylated active agent in an aqueous solution.

9. The active agent-functionalized silk material of claim 7, wherein the functionalized silk fibroin is a silk fibroin-biotin-avidin-biotin-active agent conjugate prepared via an avidin-biotin interaction between a silk fibroin-biotin conjugate and an avidin-biotinylated active agent in an aqueous solution.

10. The silk material of claim 7, wherein the silk material is a gel, film, porous scaffold, sponge, nanoparticle, or microparticle.

11. The method of claim 1, wherein the silk fibroin molecule comprises a silk microsphere or nanosphere.

12. The method of claim 1, wherein the silk fibroin molecule comprises a silk film or diazo-silk film.

13. The method of claim 1 or 2, wherein avidin or biotin is linked to the silk fibroin protein molecule via a carbodiimide coupling reaction using 1-Ethyl-3-(3-dimethylaminopropyl)-carbodiimide (EDC).

14. The method of claim 1 or 2, further comprising the step of contacting said functionalized silk with a cell.

* * * * *

UNITED STATES PATENT AND TRADEMARK OFFICE
CERTIFICATE OF CORRECTION

PATENT NO. : 8,293,486 B2  
APPLICATION NO. : 13/381687  
DATED : October 23, 2012  
INVENTOR(S) : David L. Kaplan, Xiaoqin Wang and Monica A. Serban Page 1 of 1

It is certified that error appears in the above-identified patent and that said Letters Patent is hereby corrected as shown below:

Col. 1, Line 14-15 should read

GOVERNMENT SUPPORT

This invention was made with government support under grant EB002520 awarded by the National Institutes of Health. The government has certain rights in the invention.

Signed and Sealed this
Eleventh Day of December, 2012

David J. Kappos
*Director of the United States Patent and Trademark Office*